United States Patent [19]

Hamashima et al.

[11] Patent Number: 4,731,361
[45] Date of Patent: Mar. 15, 1988

[54] ALKENEAMIDOCEPHALOSPORIN ESTERS

[75] Inventors: Yoshio Hamashima, Kyoto; Koji Ishikura; Kyoji Minami, both of Nara; Tadatoshi Kubota; Tadashi Yoshida, both of Osaka, all of Japan

[73] Assignee: Shionogi & Co., Ltd., Osaka, Japan

[21] Appl. No.: 845,305

[22] Filed: Mar. 27, 1986

[30] Foreign Application Priority Data

Mar. 29, 1985 [JP] Japan .................................. 60-67280

[51] Int. Cl.⁴ .................. C07D 501/20; A61K 31/545
[52] U.S. Cl. ..................................... 514/202; 540/222
[58] Field of Search ................ 514/202, 204; 540/222, 540/227

[56] References Cited

U.S. PATENT DOCUMENTS

| | | | |
|---|---|---|---|
| 4,416,880 | 11/1983 | Boberg et al. | 514/210 |
| 4,500,716 | 2/1985 | Kinast | 540/227 |
| 4,626,535 | 12/1986 | Angerbauer et al. | 540/222 |
| 4,632,918 | 12/1986 | Angerbauer et al. | 514/202 |
| 4,634,697 | 6/1987 | Hamashima et al. | 540/222 |
| 4,680,390 | 7/1987 | Ochiai et al. | 540/222 |

*Primary Examiner*—Donald G. Daus
*Assistant Examiner*—Barbara Cassatt
*Attorney, Agent, or Firm*—Wenderoth, Lind & Ponack

[57] ABSTRACT

An oral antibacterial, 7beta-[(Z)-2-(2-aminothiazol-4-yl)-2-alkenoylamino]-3-cephem-4-carboxylic acid pharmaceutically acceptable ester represented by the following formula:

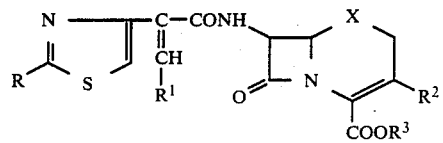

(wherein
R is amino or protected amino,
$R^1$ is straight, branched, or cyclic alkyl optionally substituted by alkoxy,
$R^2$ is hydrogen or a 3-substitutent of cephalosporins,
$R^3$ is a pharmaceutically acceptable ester group, and
X is sulfur or sulfinyl).

17 Claims, No Drawings

ALKENEAMIDOCEPHALOSPORIN ESTERS

This invention relates to 7beta-[2-(2-amino-4-thiazolyl)-2-alkenoylamino]-3-cephem-4-carboxylic acid pharmaceutically acceptable esters represented by the following formula:

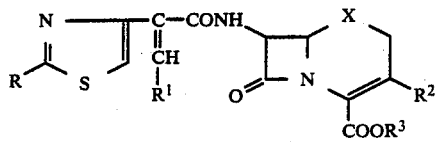

(wherein R is amino or protected amino,
$R^1$ is straight, branched, or cyclic alkyl optionally substituted by alkoxy,
$R^2$ is hydrogen or a 3-substituent of cephalosporins,
$R^3$ is a pharmaceutically acceptable ester group, and
X is sulfur or sulfinyl)

The following explains the variable groups in the formula (I).

The amino protecting group in the protected amino R can be 1C to 8C alkanoyl or substituted alkanoyl (e.g., formyl, acetyl, chloroacetyl, trifluoroacetyl), 7C to 20C aralkyl or substituted aralkyl (e.g., benzyl, diphenylmethyl, trityl, methoxybenzyl, nitrobenzyl, methylbenzyl), 1C to 8C substituted alkyl (e.g., trichloromethyl, trichloroethyl, tetrahydropyranyl), substituted arylthio, 1C to 8C alkylidene or substituted alkylidene, 7C to 14C aralkylidene or substituted aralkylidene (e.g., benzylidene, nitrobenzylidene), acyl [2C to 12C alkoxycarbonyl or substituted alkoxycarbonyl (in which the alkyl part can be methyl, ethyl, propyl, cyclopropylethyl, isopropyl, butyl, pentyl, hexyl, isobutyl, trichloroethyl, pyridylmethyl, cyclopentyl, cyclohexyl), 8C to 15C aralkoxycarbonyl or substituted aralkoxycarbonyl (in which the aralkyl part can be benzyl, diphenylmethyl, nitrobenzyl), dibasic acid acyl, and the like], trialkylsilyl, trialkylstannyl, acid addition salt group consisting of an amino group and an acid molecule, and the like which are well known in the art. One or two of the protecting groups can combine with the amino group.

The alkyl $R^1$ can preferably be 1C to 8C (especially 1C to 5C) straight, branched, or cyclic alkyl optionally substituted by 1C to 5C alkoxy. Preferably, $R^1$ is methyl, ethyl, propyl, isopropyl, cyclopropyl, t-butyl, cyclopropylmethyl, cyclopentyl, cyclopentylmethyl, cyclohexyl, and methoxymethyl.

The 3-substituent of cephalosporins $R^2$ can be a well known 3-substituent of cephalosporins, e.g., hydroxy, 1C to 5C alkanoyloxy, halogen, 1C to 5C alkoxy, 1C to 5C alkylthio, 1C to 5C alkenylthio, 1C to 5C alkyl, 1C to 5C alkenyl, heterocyclic thio containing 1 to 4 hetero atom(s) selected from nitrogen, oxygen, or sufur (especially, triazolylthio, tetrazolylthio, oxadiazolylthio, thiadiazolylthio each may have e.g., 1C to 5C alkyl, alkoxy, substituted methyl), substituted methyl or the like. Here, the substituent in the said substituted methyl can preferably be pyridinium, substituted pyridinium, halogen, hydroxy, 1C to 5C alkoxy, 1C to 5C acyloxy, 1C to 5C alkylthio, 1C to 5C haloalkylthio, 1C to 5C cyanoalkylthio, heterocyclic thio, or the like as given above. The substituent on the said substituted alkyl or the like can preferably be hydroxy, halogen, dimethylamino, carboxy, carbamoyl, etc. Preferably, $R^2$ is hydrogen, halogen, methoxymethyl, propoxymethyl, isopropyloxymethyl, propenyloxymethyl, fluoroethoxymethyl, acetoxymethyl, carbamoyloxymethyl, 1,2,3-thiadiazol-5-ylthiomethyl, 2-methyl-1,3,4-thiadiazol-5-ylthiomethyl, 2-amino-1,3,4-thiadiazol-5-ylthiomethyl, or 1-(2-hydroxyethyl)tetrazol-5-ylthiomethyl.

The phamaceutically acceptable ester group $R^3$ can be a group showing strong antibacterial potency on enteral or parenteral administration. Preferably, $R^3$ can be a 2C to 15C ester groups, especially substituted alkyl ester, for example, straight, branched, cyclic or partially cyclic alkanoyloxyalkyl ester (e.g., acetoxymethyl ester, acetoxyethyl ester, pivaloyloxymethyl ester, pivaloyloxyethyl ester, cyclohexaneacetoxyethyl ester) or alkoxyformyloxyalkyl ester (e.g., ethoxycarbonyloxyethyl ester), alkoxyalkyl ester, 2-oxacycloalkyl ester, 2-oxo-1,3-dioxolylmethyl ester, (e.g., 4-methyl-2-oxo-1,3-dioxol-5-ylmethyl ester), or the like 1-oxygenated-1C to 12C-alkyl esters); substituted aralkyl ester (e.g., phenacyl ester, phthalidyl ester); aryl ester (e.g., phenyl ester, tolyl ester, xylyl ester, indanyl ester); or the like.

Some of the free acids of compound (I) and related compounds are claimed in Japanese Patent Application Kokai No. 57-93982, etc., but no pharmaceutically acceptable ester is disclosed. The present inventors found exceedingly high oral availability of the esters and were led to this invention.

The compounds (I) are antibacterials against aerobic and anaerobic bacteria and are useful as an oral medicine. Especially characteristic features of compounds (I) are antibacterial potency against Gram-positive and Gram-negative bacteria, remarkable oral availability, excretion, distribution, etc. For the prevention or treatment of human infections, compound (I) is formulated by a conventional method and administered usually at a daily dose of 0.1 to 6 g (injection), 0.5 to 5 g (oral preparation), or 0.01 to 100 mg (topical or suppository preparation). The formulation may contain various additives, other antibacterials, or the like. Further, compound (I) may be used as a starting material for producing other antibacterials or as a material for testing the sensitivity of bacteria. The compound (I) having a protecting group is also useful as an intermediate for producing the said antibacterial compound (I).

Both of the geometric isomers at the double bond in the 7-side chain are antibacterials, but, among them, the isomer having the amido bond and $R^1$ group in cis position is a more potent antibacterial. The trans isomer is also useful as a starting material for producing the cis isomer.

Among the compounds (I), preferable ones from the viewpoint of oral availability are those having methyl, ethyl, propyl, isopropyl, or cyclopropyl as $R^1$, pivaloyloxmethyl, or acetoxymethyl as $R^3$, and propenyloxymethyl, fluoroethoxymethyl, methoxymethyl, isopropoxymethyl, carbamoyloxymethyl, hydrogen, or chloro as $R^2$.

Specific examples of preferable compounds include:
7beta-[2-(2-amino-4-thiazolyl)-2-pentenoylamino]-3-(2-propenyl)oxymethyl-3-cephem-4-carboxylic acid pivaloyloxymethyl ester,
7beta-[2-(2-amino-4-thiazolyl)-2-pentenoylamino]-3-(2-fluoroethyl)oxymethyl-3-cephem-4-carboxylic acid pivaloyloxymethyl ester,
7beta-[2-(2-amino-4-thiazolyl)-2-pentenoylamino]-3-methoxymethyl-3-cephem-4-carboxylic acid pivaloyloxymethyl ester, 7beta-[2-(2-amino-4-thiazolyl)-2-pentenoylamino]-3-isopropoxymethyl-3-cephem-4-carboxylic acid pivaloyloxymethyl ester, 7beta-[2-(2-amino-4-thiazolyl)-2-butenoylamino]-3-carbamoyloxymethyl-3-cephem-4-carboxylic acid pivaloyloxymethyl ester, 7beta-[2-(2-amino-4-thiazolyl)-2-pentenoylamino]-3-cephem-4-carboxylic acid pivaloyloxymethyl ester, 7beta-[2-(2-amino-4-thiazolyl)-2-butenoylamino]-3-carbamoyloxymethyl-3-cephem-4-carboxylic acid pivaloyloxymethyl ester, 7beta-[2-(2-amino-4-thiazolyl)-2-pentenoylamino]-3-cephem-4-carboxylic acid acetoxymethyl ester, 7beta-[2-(2-amino-4-thiazolyl)-2-butenoylamino]-3-cephem-4-carboxylic acid pivaloyloxymethyl ester, 7beta-[2-(2-amino-4-thiazolyl)-3-cyclopropyl-2-propenoylamino]-3-cephem-4-carboxylic acid pivaloyloxymethyl ester, 7beta-[2-(2-amino-4-thiazolyl)-2-pentenoylamino]-3-chloro-3-cephem-4-carboxylic acid pivaloyloxymethyl ester, 7beta-[2-(2-amino-4-thiazolyl)-4-methyl-2-pentenoylamino]-3-cephem-4-carboxylic acid pivaloyloxymethyl ester, 7beta-[2-(2-amino-4-thiazolyl)-2-hexenoylamino]-3-cephem-4-carboxylic acid pivaloyloxymethyl ester, 7beta-[2-(2-amino-4-thiazolyl)-3-cyclopentyl-2-propenoylamino]-3-cephem-4-carboxylic acid pivaloyloxymethyl ester, and 7beta-[2-(2-amino-4-thiazolyl)-2-pentenoylamino]-3-(1,2,3-thiadiazol-5-yl)thiomethyl-3-cephem-4-carboxylic acid pivaloyloxymethyl ester.

The compound (I) having a protecting group is useful also as an intermediate for producing the said antibacterial compound (I).

The compounds of this invention can, for example, be produced as follows. Generally, protection and deprotection of a functional group (e.g., amino, hydroxy) in compounds (I) can be done conventionally according to a method described in various literature references including patent publications.

(1) Amidation

The amine (II) or its reactive derivative is reacted with carboxylic acid (III) or its reactive derivative in a conventional manner to give the objective compound (I) or its derivatives.

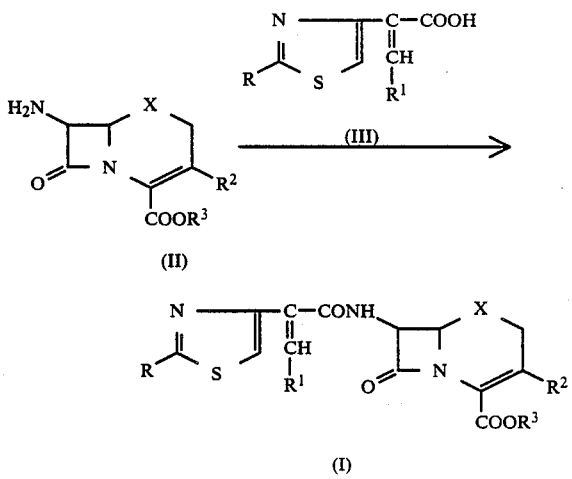

A typical reactive derivative of amine (II) have 7-amino activated by silyl (e.g., trimethylsilyl, methoxydimethylsilyl, t-butyldimethylsilyl), stannyl (e.g., trimethylstannyl), alkylene (as a part of enamino of the amino with (e.g., aldehyde, acetone, acetylacetone, acetoacetate ester, acetoacetonitrile, acetoacetanilide, cyclopentanedione, acetylbutyrolactone), alkylidene (e.g., 1-haloalkylidenne, 1-haloaralkylidene, 1-alkoxyalkylidene, 1-alkoxyaralkylidene, 1-alkoxy-1-phenoxyalkylidene, alkylidene, aralkylidene), acid (as a salt of the amino with, e.g., mineral acid, carboxylic acid, sulfonic acid), easily removable acyl (e.g., alkanoyl), or the like and that protected at other functions of the molecule.

Carboxylic acid (III) is used in the presence of a condensing reagent [carbodiimide (e.g., N,N'-diethylcarbodiimide, N,N'-dicyclohexylcarbodiimide, carbonyl compound (e.g., carbonyldiimidazole), isoxazolinium salt, acylamino compound (e.g., 2-ethoxy-1-ethoxycarbonyl-1,2-dihydroquinoline), or the like]. The reactive derivative includes acid anhydride (e.g., symmetric anhydride, mixed anhydride [with a mineral acid (e.g., phosphoric acid, sulfuric acid, carbonic half ester), organic acid (e.g., alkanoic acid, aralkanoic acid, sulfonic acid)], intramolecular acid anhydride (e.g., isocyanate, ketene), acid halide (i.e., a mixed anhydride of the acid with hydrogen halide), acid halide, reactive ester [enol ester (e.g., vinyl ester, isopropenyl ester), aryl ester (e.g., phenyl ester, halophenyl ester, nitrophenyl ester), heterocyclic ester (e.g., pyridyl ester, 1-hydroxybenzotriazolyl ester), ester with N-hydroxy compound, diacylhydroxylamine ester (ester with e.g., N-hydroxysuccinimide, N-hydroxyphthalimide), thiol ester (e.g., aralkylthiol ester, heterocyclic thiol ester), or the like], reactive amide [e.g., aromatic amide (e.g., amide with imidazole, triazole, 2-ethoxy-1,2-dihydroquinoline), diacylanilide], and the like. The acid scavenger to be used with the said reactive derivatives include an inorganic base (e.g., oxide, hydroxide, carbonate, hydrogen carbonate, or the like or alkali metal, alkaline earth metal), organic base (e.g., tertiary amine, aromatic base,), oxirane (e.g., alkylene oxide, aralkylene oxide), pyridinium salt (e.g., tripyridiniumtriazine trichloride), adsorbent (e.g., Celite), and the like.

(2) Introduction of the 3-substituent

Compound (I) but having a leaving group-substituted methyl at position 3 is treated with a hetero aromatic thiol, aromatic base, or reactive derivative thereof giving objective compound (I). Halogen, sulfonyloxy, alkanoyloxy, dihaloacetoxy, trihaloacetoxy, and the like are the typical leaving groups. An alkali metal salt, ammonium salt, carboxylate ester, and the like are typical reactive derivatives of the thiol. The reaction proceeds at 0° C. to 60° C. even in an anhydrous or aqueous solvent. This reaction is promoted by a dehydrating reagent, phosphoryl chlorides, thiocyanates, or the like.

Compound (I) having alkanoyloxymethyl or carbamoyloxymethyl at position 3 is prepared from compound (I) but having hydroxymethyl at position 3 and protected carboxy at position 4 by treating with a reactive derivative of alkanoic acid or N-protected carbamic acid, and if required, deprotected at the stage where the objective group can remain in the target compound.

Compound (I) having no carbon atom attached to position 3 can be prepared by the reaction of 3-(hydroxy or oxo)-compound (if required, after activation by acylation, halogenation, or the like) with a nucleophilic reagent, etc. to give a 3-nucleophilic group substituted compound; or by elimination reaction of 3-(hydroxy, acyloxy, or halo)cepham compound by heat or with base; reduction of a 3-(acyloxy or halo)-3-cephem compound giving 3-unsubstituted compound; or the like each in a conventional method.

(3) Isomerization at position 7 side chain

Each geometric isomer of Compound (I) can be transformed into the other. This reaction is taken place by the action of acid, base or light. Here, the said acid includes a mineral acid (e.g., hydrochloric acid, sulfuric acid, phosphoric acid), carboxylic acid (e.g., formic acid, trifluoroacetic acid), sulfonic acid (e.g., methanesulfonic acid, benzenesulfonic acid), etc.; the said base includes an inorganic base (e.g., sodium hydroxide, sodium hydrogen carbonate, potassium carbonate), strong organic base (e.g., triethylamine, potassium t-butoxide, DBU), etc.

(4) Esterification of carboxy

The carboxy group at position 4 can be esterified by a known method, for example, (a) A reaction of an alkali metal salt of the carboxylic acid with a halide, sulfonate, or the like of the ester group in the presence of an acid scavenger. (b) A reaction of the carboxylic acid or its reactive derivative with alcohol having the ester group in the presence of a condensing reagent. (c) A reaction of the carboxylic acid with a diazo compound having the ester group.

(5) Introduction of an amino-protecting group

When Compound (I) has amino in its molecule, the amino can be protected by using, for example, as follows: (a) an alkoxycarbonyl, aralkoxycarbonyl, alkanoyl, etc., group is introduced by reacting 1 to 5 molar equivalents of halide, symmetric anhydride, or mixed anhydride of these groups in the presence of an acid scavenger at −30° to 50° C.; (b) an alkoxycarbonyl, aralkoxycarbonyl, alkanoyl, arylsulfenyl, aralkyl, trialkylsilyl, trialkylstannyl, etc., group is introduced by reacting 1 to 5 molar equivalents of halide of the group in the presence of 1 to 10 molar equivalents of an acid scavenger in a solvent at −30° to 100° C. for 1 to 10 hours; (c) a tetrahydropyranyl, tetrahydrofuranyl, etc., group is introduced by the reaction with dihydropyran, dihydrofuran, etc., in a solvent for 1 to 10 hours. (d) a trialkylsilyl group is introduced by the reaction with a derivative of disilazane, acetamido, or the like (e.g., hexamethyldisilazane, bistrimethylsilylacetamide), in a conventional manner.

(6) Deprotection of protected amino as R

A protected amino group in compound (I) can be deprotected, for example, by the following convetional methods: (a) an alkoxycarbonyl group (e.g., tert-butoxycarbonyl), can be deprotected by reacting with an acid, for example, a strong acid (e.g., trifluoroacetic acid, trifluoromethanesulfonic acid), or Lewis acid (e.g., aluminum chloride, tin chloride, titanium chloride, zinc chloride), if required in the presence of a cation scavenger (e.g., anisole, benzenethiol); (b) an aralkoxycarbonyl group (e.g., carbobenzoxy, methylcarbobenzoxy, diphenylmethoxycarbonyl) or the like amino protecting group can be deprotected by reacting with a Lewis acid and a cation scavenger as given above; (c) a lower alkanoyl group (e.g., formyl, acetyl, chloroacetyl), Schiff base forming group, i.e., a divalent carbon group (e.g., ethylidene, propylidene, benzylidene, substituted benzilidene), aralkyl (e.g., trityl, substituted trityl), arylthio (e.g., phenylsulfenyl), tetrahydropyranyl, silyl or stannyl (e.g., trimethylstannyl, trimethylsilyl), and other ones are deprotected by reacting with acid (e.g., hydrochloric acid, sulfuric acid, methanesulfonic acid); and (d) some protecting group has its specific method for deprotection (e.g., the reaction of thiourea or N-alkyldithiocarbamate for haloacetyl, hydrazine for a dibasic acid acyl, and phosphorus pentachloride and alkanol for amide).

(7) Sulfoxide formation

Compound (I) having sulfide group is oxidized, for example, by the following conventional methods. In this case, when the starting material has 2-double bond, the latter migrates to the position 3. (a) peracid (an industrially available per-mineral acid, percarboxylic acid, persulfonic acid, etc.); (b) ozone; (c) hydrogen peroxide; and (d) peroxide (e.g., boron peroxide, nickel peroxide, sodium peroxide, urea peroxide) preferably in an inert solvent (e.g., halohydrocarbon, ester, water) to give the corresponding sulfoxide (I). These reactions may be accelerated with (e.g., phosphoric acid, polyphosphoric acid, phosphoric acid monoester, alkanoic acid, acid salts of Group VII atoms in the Periodic Table, e.g., tungstates). The reaction is preferably carried out with 1 to 2 molar equivalents of an oxidizing reagent at 0° to 35° C. for 1 to 20 hours.

(8) Reduction of the sulfoxide

When compound (I) has sulfinyl in the molecule (e.g., when X is SO), it can be reduced by a conventional method to give the corresponding sulfide (I), for example, with 2 to 5 molar equivalents of a reducing reagent (e.g., trivalent phosphorus compund, stannous salt, iodide) in an inert solvent (e.g., dimethylformamide, dichloromethane, dioxane) at −20° to 50° C. for 2 to 50 hours.

(9) Reaction conditions

The reactions from (1) to (8) are usually carried out at −30° C. to 100° C. (preferably at −20° C. to 50° C.) for 10 minutes to 10 hours in a solvent, if required in a dry condition. Other conventional conditions may be applied to the reactions.

The typical reaction solvent can be a hydrocarbon (e.g., pentane, hexane, octane, benzene, toluene, xylene), halohydrocarbon (e.g., dichloromethane, chloroform, carbon tetrachloride, dichloroethane, trichloroethane, chlorobenzene), ether (e.g., diethyl ether, methyl isobutyl ether, dioxane, tetrahydrofuran), ketone (e.g., acetone, methyl ethyl ketone, cyclohexanone), ester (e.g., ethyl acetate, isobutyl acetate, methyl benzoate), nitrohydrocarbon (e.g., nitromethane, nitrobenzene), nitrile (e.g., acetonitrile, benzonitrile), amide (e.g., formamide, acetamide, dimethylformamide, dimethylacetamide, hexamethylphosphorotriamide), sulfoxide (e.g., dimethyl sulfoxide), carboxylic acid (e.g., formic acid, acetic acid, propionic acid), organic base (e.g., diethylamine, triethylamine, pyridine, picoline, collidine, quinoline), alcohol (e.g., methanol, ethanol, propanol, hexanol, octanol, benzyl alcohol), water, or other industrial solvent or a mixture of two or more of these.

(10) Work up

The objective products are recovered from the reaction mixture by removing a contaminant (e.g., unreacted starting materials, by-products, solvents) by a conventional method (e.g., extraction, evaporation, washing, concentration, precipitation, filtration, drying), and by a combination of conventional purification (e.g., adsorption, elution, distillation, precipitation, separation, chromatography).

(11) Examples

The following examples illustrate the embodiment of this invention. The physical constants of the products are listed on the tables. In the tables, IR shows cm$^{-1}$ values and NMR shows delta values in ppm and J values showing coupling constants in Hz values.

In Tables 1 and 2, all compounds have R$^1$ and amido groups in cis positions.

In the exampls, "part" shows weight per weight of starting beta-lactams and "molar equivalent" shows mole number per starting beta-lactams.

Work-up of the examples are done usually (if required after adding a solvent e.g., water, acid, dichloromethane) and the separated organic layer is washed with water, dried, and vacuum-distilled giving residue which may be purified conventionally (e.g., by chromatography over silica gel, crystallization, precipitation).

EXAMPLE 1

A 7beta-amino compound (2) (1 equivalent) is treated with carboxylic acid corresponding to the 7beta-side chain (3) or its reactive derivative to give the corresponding amide (1), for example, by an acylation represented by the following equation and as exemplified below:

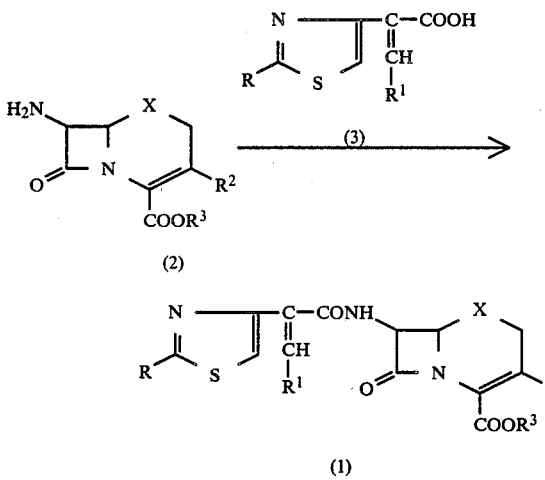

(1) In a mixture of dichloromethane (30 volumes), cyanuric chloride (1.1 equivalents), pyridine (4 equivalents), and carboxylic acid (3) (1.1 equivalents), stirred for 5 minutes to 2 hours at −30° C. to 10° C.

(2) In a mixture of dichloromethane (3 volumes), phosphorus oxychloride (1.1 equivalents), triethylamine (1.5 equivalents), and carboxylic acid (3) (1.1 equivalents), stirred for 20 minutes to 2 hours at −10° C. to 10° C.

(3) In a mixture of chloroform (3 volumes), toluene (1 volume), picoline (2 equivalents), oxalyl chloride (1 equivalent), and carboxylic acid (3) (1.1 equivalents), stirred for 10 minutes to 2 hours at −50° C. to 10° C.

(4) To a solution of 2-(2-t-butoxycarbonylcarbonylaminothiazol-4-yl)-2-pentenoic acid (149 mg), triethylamine (83 microliter) in dichloromethane (5 ml) is added methanesulfonyl chloride (0.04 ml) at −60° C. After stirring at the same temperature for 2 hours, a solution of 7beta-amino-3-cephem-4-carboxylic acid 1-acetoxyethyl ester (161 mg) and N-methylmorpholine (0.132 ml) in dichloromethane is added dropwise to the reaction mixture. The mixture is stirred at −60° to −10° C. for 3 hours, diluted with hydrochloric acid, and separated to obtain organic layer. The layer is washed with water, dried, and purified by column chromatography to give 7beta-[(Z)-2-(2-t-butoxycarbonylaminothiazol-4-yl)-2-pentenoyl]amino-3-cephem-4-carboxylic acid 1-acetoxyethyl ester (470 mg).

(5) In a manner similar to that of above (1) to (4), the compounds listed on Table 2 are prepared.

EXAMPLE 2 (Amino deprotection)

(1) To a solution of a tertiary butoxycarbonylamino compound of Table 2 in dichloromethane (0.3 to 3 parts) are added tri-fluoroacetic acid (0.3 to 3 parts) and anisole (0.5 to 5 parts). The mixture is stirred at −10° to 40° C. for 10 minutes to 3 hours. The reaction mixture is concentrated to remove the solvent and reagents, and the resulting residue is washed with benzene or ether to give the corresponding amino compound in Table 1. Yield: 70 to 80%.

(2) To a solution of a chloroacetamido compound on Table 2 in a mixture of tetrahydrofuran (15 parts) and methanol (15 parts) are added thiourea or N-methyldithiocarbamate ester (4 equivalents) and sodium acetate (2 equivalents), and the mixture is kept at room temperature overnight. The mixture is concentrated, diluted with ethyl acetate, washed with water, dried, and concentrated to give the corresponding amino compound on Table 1.

(3) To a solution of a formamido or Schiff base compound of Table 2 in formic acid, acetic acid, or ethanol (10 parts) is added 1 to 3N-hydrochloric acid (0.1 to 3 parts), and the mixture is stirred at room temperature for 1 to 3 hours. The reaction mixture is concentrated, diluted with dichloromethane, washed with aqueous sodium hydrogen carbonate and water, dried, and concentrated to give the corresponding amino compound on Table 1.

(4) To a solution of a formylamino, tertiary butoxycarbonylamino, or benzyloxycarbonylamino compound on Table 2 in dichloromethane (5 to 9 parts) are added anisole (2 to 8 parts) and aluminum chloride, titanium tetrachloride, or tin tetrachloride (1 to 3 equivalents), and the mixture is stirred at −35° to 10° C. for 10 minutes to 24 hours. The reaction mixture is extracted with diluted hydrochloric acid. The extract solution is passed through a column of adsorbent to remove salts, and eluate is concentrated to give the corresponding amino compound on Table 1.

(5) A solution of 7beta-[(Z)-2-(2-t-butoxycarbonylaminothiazol-4-yl)-2-butenoyl]amino-3-carbamoyloxymethyl-3-cephem-4-carboxylic acid pivaloyloxymethyl ester (160 mg) in trifluoroacetic acid (2 ml) is stirred at room temperature for 120 minutes and concentrated. To the resulting residue is added aqueous sodium hydrogen carbonate and extracted with ethyl acetate. The extract solution is purified by silica gel chromatography to give 7beta-[(Z)-2-(2-aminothiazol-4-yl)-2-butenoyl]amino-3-carbamoyloxymethyl-3-cephem-4-carboxylic acid pivaloyloxymethyl ester (75 mg).

(6) In a manner similar to above (1) to (5), amino compounds on Table 1 are synthesized from the corresponding protected amino compounds.

EXAMPLE 3

(Esterification)

(pivaloyloxymethyl ester)

(1) To a solution of a potassium salt of a carboxylic acid in N,N-dimethylformamide (2 to 5 parts) is added iodomethyl pivalate (1 to 2 equivalents) at −50 to room temperature. After stirring for 15 minutes to 2 hours, the mixture is diluted with ethyl acetate, washed with ice water and aqueous sodium hydrogen carbonate, dried, and concentrated. The residue is crystallized from ethyl acetate to give the pivaloyloxymethyl ester. This pivaloyloxymethyl ester (250 mg), corn starch (150 mg), and magnesium stearate (5 mg) are mixed, granulated, and encapsulated in a conventional manner. This capsule (2 to 3 capsules) is given orally thrice a day to treat a patient suffering from an infection caused by Escherichia coli.

In a similar manner, pivaloyloxymethyl compounds listed on Table 2 are prepared.

(acetoxymethyl ester)

(2) In place of iodomethyl pivalate of above (1), bromomethyl acetate is used under the same condition to give the corresponding acetoxyethyl ester.

In a similar manner, acetoxymethyl compounds listed on Table 2 are prepared.

(acetoxyethyl ester)

(3) In place of iodomethyl pivalate of above (1), bromoethyl acetate is used under the same condition to give the corresponding acetoxyethyl ester.

In a similar manner, acetoxyethyl compounds listed on Table 2 are prepared.

(1-pivaloyloxyethyl ester)

(4) To a soultion of 7beta-[2-(2-t-butoxycarbonylamino-4-thiazolyl)-2-pentenoylamino]-3-cephem-4-carboxylic acid (240 mg) in N,N-dimethylformamide (2.4 ml) is added potassium carbonate (138 mg) at −25° to 30° C. and the mixture is stirred for several minutes. To the mixture is added pivaloyloxyethyl iodide (480 microliter) and the mixture is stirred for 60 minutes. The reaction mixture is diluted with ethyl acetate, washed with aqueous saline and sodium hydrogen carbonate, and water, dried and concentrated. The residue is chromatographed over silica gel to give the corresponding pivaloyloxyethyl ester (161 mg). Yield. 53%.

In a similar manner, pivaloyloxyethyl esters listed on Table 2 are prepared.

(ethoxycarbonyloxyethyl ester)

(5) To a solution of 7beta-[2-(2-t-butoxycarbonylamino-4-thiazolyl)-2-pentenoylamino]-3-cephem-4-carboxylic acid (240 mg) in N,N-dimethylformamide (2.4 ml) is added potassium carbonate (138 mg) and 1-ethoxycarbonyloxyethyl bromide (150 mg) at −10° C. After stirring for 30 minutes, the mixture is diluted with ethyl acetate, washed with aqueous saline and sodium hydrogen carbonate, and water, dried and concentrated. The residue is chromatographed over silica gel to give the corresponding ethoxycarbonyloxyethyl ester (191 mg). Yield. 64.1%.

In a similar manner, ethoxycarbonyloxyethyl esters listed on Table 2 are prepared.

(5-methyl-2-oxo-1,3-dioxol-3-en-4-ylmethyl ester)

(6) A mixture of 7beta-[(Z)-2-(2-t-butoxycarbonylaminothiazol-4-yl)-2-pentenoyl]amino-3-cephem-4-carboxylic acid (144 mg), potassium carbonate (83 mg), and dimethylformamide (3 ml) is stirred for 40 minutes at room temperature and mixed with 4-bromomethyl-5-methyl-1,3-dioxol-4-en-2-one (102 mg) in dimethylformamide (1 ml). After stirring at 0° C. for 30 minutes, the mixture is diluted with aqueous hydrochloric acid and extracted with ethyl acetate. The extract is purified by silica gel chromatography to give 7beta-[(Z)-2-(2-t-butoxycarbonylaminothiazol-4-yl)-2-pentenoyl]amino-3-cephem-4-carboxylic acid 5-methyl-2-oxo-1,3-dioxol-4-en-4-ylmethyl ester (83 mg) as pale yellow powder.

(cyclohexaneacetoxyethyl ester)

(7) To a solution of 7beta-[2-(2-t-butoxycarbonylamino-4-thiazolyl)-2-pentenoylamino]-3-cephem-4-carboxylic acid (240 mg) in N,N-dimethylformamide (2.4 ml) is added potassium carbonate (138 mg) and 1-cyclohexaneacetoxyethyl iodide (355 mg) at −10° C. After stirring for 45 minutes, the mixture is diluted with ethyl acetate, washed with aqueous saline and sodium hydrogen carbonate, and water, dried and concentrated. The residue is chromatographed over silica gel to give the corresponding cyclohexaneacetoxyethyl ester (152 mg).

In a similar manner, cyclohexaneacetoxyethyl esters listed on Table 2 are prepared.

(8) In a manner similar to above, pharmacological esters on Table 2 can be prepared from the corresponding carboxylic acid.

EXAMPLE 4

(Sulfoxide formation)

(1) A sulfide is stirred with aqueous 30% hydrogen peroxide (1 equivalent) in a mixture of phosphoric acid (1 equivalent), dichloromethane (17 parts), and methanol (1 part) under ice cooling for 10 minutes to give the corresponding sulfoxide.

(2) To a solution of 7beta-[(Z)-2-(2-t-butoxycarbonylaminothiazol-4-yl)-2-pentenoyl]amino-3-chloro-2-cephem-4-carboxylic acid pivaloyloxymethyl ester (410 mg) in dichloromethane (3 ml) is added dropwise a solution of m-chloroperbenzoic acid (47.4 mg) in dichloromethane (1 ml) with stirring at 0° C. After stirring at the same temperature for 20 minutes, the reaction mixture is diluted with aqueous sodium hydrogen carbonate. The organic layer is separated, washed with water, dried, and concentrated. The resulting residue is purified by silica gel column chromatography to give 7beta-[(Z)-2-(2-t-butoxycarbonylaminothiazol-4-yl)-2-pentenoyl]amino-3-chloro-3-cephem-4-carboxylic acid 1-oxide pivaloyloxymethyl ester (135 mg) as crystals.

EXAMPLE 5

(Sulfoxide reduction)

(1) to a solution of 7beta-[(Z)-2-(2-t-butoxycarbonylaminothiazol-4-yl)-2-penteoyl]amino-3-cephen-4-carboxylic acid 1-oxide pivaloyloxymethyl ester (61 mg) in dichloromethane (2 ml) is added phosphorus tribromide (19.3 microliter) at −30° C. and the mixture is stirred for 30 minutes. The reaction mixture is diluted with aqueous sodium hydrogen carbonate. The organic layer is separated, washed with water, dried, and concentrated. The residue is purified by silica gel column chromatography to give 7beta-[(Z)-2-(2-t-butoxycarbonylaminothiazol-4-yl)-2-pentenoyl]amino-3-cephem-4-carboxylic acid pivaloyloxymethyl ester (51 mg).

(2) In the reaction condition of above 1), phosphorus tribromide in dichloromethane at −30° C. for 30 minutes is substituted by potassium iodide (6 molar equivalents) in acetone (11 parts) for 1 hour under ice cooling or acetyl chloride (13 equivalents) and stannous chloride (2.5 molar equivalents) in N,N-dimethylformamide (12 parts) under ice cooling for 21 hours to give the same sulfide.

(3) In a manner similar to above, sulfides on Table 1 or Table 2 can be prepared by reducing the corresponding sulfoxides.

EXAMPLE 6

(Acid addition salt)

(1) [trifluoroacetate] A solution of 7beta-[(Z)-2-(2-t-butoxycarbonylaminothiazol-4-yl)-2-pentenoyl]amino-3-carbamoyloxymethyl-3-cephem-4-carboxylic acid pivaloyloxymethyl ester (450 mg) in trifluoroacetic acid (5 ml) is stirred at room temperature for 120 minutes and then concentrated. The residue is diluted with aqueous sodium hydrogen carbonate and extracted with ethyl acetate. The extract is purified by silica gel chromatography to give the corresponding free amine. This is dissolved in dichloromethane (4 ml), mixed with trifluoroacetic acid (1 ml), and vacuum-concentrated. The crystalline residue is triturated in a mixture of ether and petroleum ether to give 7beta-[(Z)-2-(2-aminothiazol-4-yl)-2-pentenoyl]amino-3-carbamoyloxymethyl-3-cephem-4-carboxylic acid pivaloyloxymethyl ester trifluoroacetate (290 mg).

(2) [Hydrochloride] A solution of 7beta-[(Z)-2-(2-t-butoxycarbonylaminothiazol-4-yl)-2-pentenoyl]amino-3-cephem-4-carboxylic acid pivaloyloxymethyl ester (360 mg) in a mixture of anisole (2 ml) and trifluoroacetic acid (2 ml) is stirred at room temperature for 150 minutes and concentrated. The residue is dissolved in aqueous sodium hydrogen carbonate and extracted with ethyl acetate. The extract is purified by silica gel column chromatography to give 7beta-[(Z)-2-(2-amino-thiazol-4-yl)-2-pentenoyl]amino-3-cephem-4-carboxylic acid pivaloyloxymethyl ester (250 mg). This is dissolved in dichloromethane, mixed with a solution of hydrochloric acid in ethyl acetate, and concentrated. The crystalline residue is washed with ether to give the hydrochloride of above ester.

(3) In a manner similar to above, acid addition salts can be prepared from the corresponding amino compounds on Table 1.

EXAMPLE 7

(1) To a solution of aminothiazolyl compound in dichloromethane is added formic acid and acetic anhydride, chloroacetyl chloride and pyridine, or nitrobenzaldehyde and toluenesulfonic acid, and the mixture is stirred at −30 to room temperature for 1 to 3 hours. The mixture is treated in a usual manner to give the corresponding amino-protected compound as shown on Table 4.

Preparation 1

To a solution of 7beta-[(Z)-2-(2-t-butoxycarbonylaminothiazol-4-yl)-2-pentenoyl]amino-3-cephem-4-carboxylic acid 1-oxide diphenylmethyl ester (265 mg) in a mixture of anisole (0.8 ml) and dichloromethane (1.5 ml) is added trifluoroacetic acid (1 ml) at 0° C. with stirring. After 45 minutes' stirring, the mixture is concentrated in vacuum. The residue is washed with petroleum ether and ether to give 7beta-[(Z)-2-(2-t-butoxycarbonylaminothiazol-4-yl)-2-pentenoyl]amino-3-cephem-4-carboxylic acid 1-oxide (180 mg).

NMR (CDCl$_3$-OD$_3$CD)δ: 1.11(t, J=7.5 Hz, 3H), 1.55(s, 9H), 2.49(quintet, J=7.5 Hz, 2H), 4.78(d, J=4.5 Hz, 1H), 6.13(d, J=4.5 Hz, 1H), 6.40(m, 1H), 6.45(t, J=7.5 Hz, 1H), 6.79(s, 1H).

Preparation 2

To a solution of 2-amino-1,3,4-thiadiazole-5-thiol (156 mg) in dimethylformamide (3 ml) is added a solution (0.3 ml) of 5.2N-sodium methoxide in methanol with stirring at 0° C. to give the sodium salt. After neutralizing excess sodium methoxide with dry ice, a solution of 7beta-[(Z)-2-(2-t-butoxycarbonylaminothiazol-4-yl)-2-pentenoyl]amino-3-bromomethyl-3-cephem-4-carboxylic acid 1-oxide diphenylmethyl ester (590 mg) in dimethylformamide (2 ml) is added to the mixture. After stirring at 0° C. for 30 minutes, the reaction mixture is poured into ice water and extracted with ethyl acetate to give crude 7beta-[(Z)-2-(2-t-butoxycarbonylaminothiazol-4-yl)-2-pentenoyl]amino-3-(2-amino-1,3,4-thiadiazol-5-ylthiomethyl)-3-cephem-4-carboxylic acid 1-oxide diphenylmethyl ester in a quantitative yield.

NMR (CDCl$_3$)δ: 1.07(t, J=8 Hz, 3H), 1.48(s, 9H), 2.52(quintet, J=8 Hz, 2H), 3.61, 3.82(ABq, J=18 Hz, 2H), 4.60, 3.70(ABq, J=18 Hz, 2H), 4.55(d, J=5 Hz, 1H), 5.60(brs, 2H), 6.15(dd, J=5 Hz, J=9 Hz, 1H), 6.40(t, J=8 Hz, 1H), 6.74(s, 1H), 6.88(s, 1H), 7.20~7.45(m, 10H), 8.83(d, J=9 Hz, 1H).

The ester group of this product is removed in a manner similar to that of Preparation 1 and the sulfoxide is reduced in a manner similar to that of Example 5-2) to give 7beta-[(Z)-2-(2-t-butoxycarbonylaminothiazol-4-yl)-2-pentenoyl]amino-3-(2-amino-1,3,4-thiadiazol-5-ylthiomethyl)-3-cephem-4-carboxylic acid.

Preparation 3

(1) To a mixture of 2-(2-t-butoxycarbonylaminothiazol-4-yl)-pentenoic acid (75 mg), triethylamine (0.041 ml), and dichloromethane (3 ml) is added dropwise methanesulfonyl chloride (0.02 ml) at −60° C. with stirring. After stirring at the same temperature for 5 hours, a solution of 7beta-amino-3-carbamoyloxymethyl-3-cephem-4-carboxylic acid diphenylmethyl ester p-toluenesulphonate salt (153 mg) and N-methylmorpholine (0.05 ml) in dichloromethane (3 ml) is added dropwise to the mixture. After stirring for 3.5 hours, the mixture is quenched with diluted hydrochloric acid. The organic layer is separated, washed with water, dried, and concentrated. The residue is purified by silica gel column chromatography to give 7beta-[(Z)-2-(2-t-butoxycarbonylaminothiazol-4-yl)-2-pentenoyl]amino-3-carbamoyloxymethyl-3-cephem-4-carboxylic acid diphenylmethyl ester (155 mg).

IR (CHCl$_3$)ν: 3430, 1785, 1726, 1672, 1543, 1326, 1158, 980.

NMR (CDCl$_3$)δ: 1.10(t, J=7.5 Hz, 3H), 1.51(s, 9H), 2.55(quintet, J=7.5 Hz, 2H), 3.16(s, 2H), 4.80, 4.97(ABq, J=14.4 Hz, 2H), 4.82(s, 2H), 4.93(d, J=4.5 Hz, 1H), 5.67(dd, J=4.5 Hz, J=8 Hz, 1H), 6.37(t, J=7.5 Hz, 1H), 6.68(s, 1H), 6.80(s, 1H), 7.22~7.40(m, 10H), 7.82(d, J=8 Hz, 1H), 10.0(brs, 1H).

(2) To an ice cold solution of 7beta-[(Z)-2-(2-t-butoxycarbonylaminothiazol-4-yl)-2-pentenoyl]amino-3-carbamoyloxymethyl-3-cephem-4-carboxylic acid diphenylmethyl ester (855 mg), anisole (3.3 ml), and dichloromethane (8.3 ml) is added trifluoroacetic acid (1.93 ml) with stirring. After reacting at the same temperature for 30 minutes, the mixture is concentrated in vacuum. The residue is washed with petroleum ether and ether to give pale brown 7beta-[(Z)-2-(2-t-butoxycarbonylaminothiazol-4-yl)-2-pentenoyl]amino-3-carbamoyloxymethyl-3-cephem-4-carboxylic acid (640 mg).

IR (CHCl$_3$)$\nu$: 3425, 3360br, 1778, 1725, 1700, 1660, 1327, 1258, 1160, 1078.

NMR (CDCl$_3$-CD$_3$OD)$\delta$: 1.07(t, J=7.5 Hz, 3H), 1.53(s, 9H), 2.41(quintet, J=7.5 Hz, 2H), 3.43, 3.61(ABq, J=19.8 Hz, 2H), 4.87, 5.10(ABq, J=14.4 Hz, 2H), 5.08(d, J=5.0 Hz, 1H), 5.85(d, J=5.0 Hz, 1H), 6.41(t, J=7.5 Hz, 1H), 6.80(s, 1H).

Experiment

Male rats weighing 20 to 25 gram are freely fed an aqueous solution of 40% glucose and vitamins instead of a chow diet for one day. Next day, a suspension of amoxicillin (the reference compound) or one of the esters (the test compounds) in aqueous 5% arabic gum having a potency of 2 mg per milliliter was orally administered at a dose of 40 mg/kg each of the reference compound or the test compounds. Then, the blood is taken at 15 minutes intervals to determine the activity in the plasma. For the determination is used *Escherichia coli* for esters and *Micrococcus luteus* for amoxicillin by the agar plate dispersion method. The results are listed on the following table.

TABLE

Maximum plasma level (gamma/ml) of Compound (I) (in which R is amino and $R^3$ = pivaloyloxymethyl) after oral administration to mice

| No. | $R^1$ | $R^2$ | maximum serum level |
|---|---|---|---|
| 1 | Me | H | 8.6 |
| 2 | Me | CH$_2$OCONH$_2$ | 13.4 |
| 3 | Et | H | 14.1 |
| 4 | Et | CH$_2$OCONH$_2$ | 9.3 |
| | amoxicillin | | 15.7 |

TABLE 1
Physical constants of pharmaceutical esters

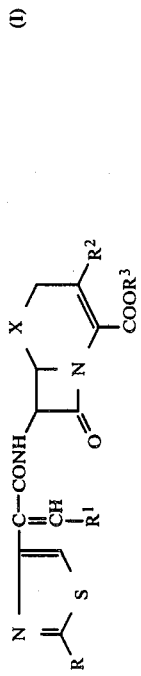

(I)

| No. | R | R¹ | R² | R³ | X | IR: $\nu$ (CHCl$_3$) cm$^{-1}$ | NMR: $\delta$ (CDCl$_3$) ppm | Example No |
|---|---|---|---|---|---|---|---|---|
| 1 | H$_2$N | Me | H | POM | S | nd. | 1.21(s, 9H), 1.93(d, J=7Hz, 3H), 3.40(dd, A of ABX, J=5Hz, J=18.9Hz, 1H), 3.60(dd, B of ABX, J=3Hz, J=18.9Hz, 1H), 5.03(d, J=5Hz, 1H), 5.80, 5.91(ABq, J=6Hz, 2H), 5.96(dd, J=5Hz, J=8Hz, 1H), 6.25(s, 1H), 6.49(q, J=7Hz, 1H), 6.59(dd, X of ABX, J=3Hz, J=5Hz, 1H), 8.40(d, J=8Hz, 1H). | (2-1),(2-4) |
| 2 | H$_2$N | Me | CH$_2$OCONH$_2$ | POM | S | 3550, 3485, 3430, 3395, 1786, 1735, 1672, 1525, 1330, 1126. | 1.21(s, 9H), 1.90(d, J=7.0Hz, 3H), 3.40, 3.52(ABq, J=18.0Hz, 2H), 4.76, 5.03(ABq, J=16.9Hz, 2H), 5.02(d, J=5.0Hz, 1H), 5.12 (s, 2H), 5.54(brs, 2H), 5.77~5.95(m, 3H), 6.22(s, 1H), 6.45(q, J=7.0Hz, 1H), 8.45(d, J=9.0Hz, 1H). | (2-5) |
| 3 | H$_2$N | Me | CH$_2$S(1,2,3-thiadiazol-5-yl) | POM | S | 3480, 3390, 1785, 1750, 1670, 1600, 1520, 1365, 1110, 990. | 1.20(s, 9H), 1.95(d, J=8Hz, 3H), 3.51, 3.62(Abq, J=15Hz, 2H), 4.06, 4.16(ABq, J=14Hz, 2H), 5.08(d, J=5Hz, 1H), 5.50(brs, 2H), 5.83(s, 2H), 5.92(dd, J=5Hz, J=8Hz, 1H), 6.28(s, 1H), 6.52(q, J=8Hz, 1H), 8.53(s, 1H), 8.63(d, J=8Hz, 1H). | (2-1) |
| 4 | H$_2$N | Et | H | AOM | S | nd | 1.05(t, J=8Hz, 3H), 2.11(s, 3H), 2.37(quintet, J=8Hz, 2H), 3.23~3.77(m, 2H), 5.02(d, J=5Hz, 1H), 5.26(s, 2H), 5.82, 5.92(ABq, J=6Hz, 2H), 5.98(dd, J=5Hz, J=9Hz, 1H), 6.32(s, 1H), 6.42(t, J=8 Hz, 1H), 6.56~6.66(m, 1H), 8.10(d, J=9Hz, 1H). | (2-1) |
| 5 | H$_2$N | Et | H | AOE | S | nd | 1.05(t, J=8.0Hz, 3H), 1.54(d, J=6.0Hz, 3H), 2.07(s, 3H), 2.36 (quintet, J=8.0Hz, 2H), 3.42(dd, A of ABX, J=7.0Hz, J=20.0Hz, 1H), 3.61(dd, B of ABX, J=4.0Hz, J=20.0Hz, 1H), 5.03(d, J=5.0Hz, 1H), 5.46(brs, 2H), 5.98(dd, J=5.0Hz, J=9.0Hz, 1H), 6.29(s, 1H), 6.42(t, J=8.0Hz, 1H), 6.58(dd, X of ABX, J=4.0Hz, J=7.0Hz, 1H), 6.99(q, J=6.0Hz, 1H), 8.19(d, J=9.0Hz, ½H), 8.26(d, J=9.0Hz, ½H). | (2-1),(3-3) |
| 6 | H$_2$N | Et | H | POM | S | 3475, 3380, 3325, 1783, 1750, 1674, 1522, 1285, 1123, 982. | 1.02(t, J=7.5Hz, 3H), 1.20(s, 9H), 2.34(dq, J=7.5Hz, 2H), 3.43(dd, A of ABX, J=7Hz, J=18.9Hz, 1H), 3.63(dd, B of ABX, J=3Hz, J=18.9Hz, 1H), 5.06(d, J=5Hz, 1H), 5.48(s, 2H), 5.84, 5.94 (ABq, J=5.4Hz, 2H), 5.97(dd, J=5Hz, J=8Hz, 1H), 6.27(s, 1H), 6.42(t, J=8Hz, 1H), 6.63(dd, X of ABX, J=3Hz, J=7Hz, 1H), 8.36 (d, J=8Hz, 1H). | (2-1),(2-2), (2-3),(2-4), (3-1),(5-2) |
| 7 | H$_2$NHCl | Et | H | POM | S | 3250, 2715br, 1782, 1747, 1660, 1627, 1278, 1123, 982. | 1.12(t, J=7.5Hz, 3H), 1.20(S, 9H), 2.37(quintet, J=7Hz, 2H), 3.75(dd, A of ABX, J=7Hz, J=19.8Hz, 1H), 3.71(dd, B of ABX, J=3.5Hz, J=19.8Hz, 1H), 5.17(d, J=5Hz, 1H), 5.82, 5.91(ABq, J=6.3 Hz, 2H), 5.92(d, J=5Hz, 1H), 6.32(t, J=7.5Hz, 1H), 6.67(dd, X of ABX, J=3.5Hz, J=7.5Hz, 1H), 6.69(s, 1H). | (6-2) |
| 8 | H$_2$N | Et | H | POE | S | nd | 1.06(t, J=8Hz, 3H), 1.20(s, 9H), 1.53(d, J=5Hz, 3H), 2.38(quintet, J=8Hz, 2H), 3.20~3.76(m, 2H), 5.02(d, J=5Hz, 1H), 5.23(brs, 2H), 5.87~6.06(m, 1H), 6.33(s, 1H), 6.42(t, J=8Hz, 1H), 6.52~6.62(m, 1H), 6.86~7.00(m, 1H), 7.96, 8.06(2Xd, J=9Hz, 1H). | (2-1) |
| 9 | H$_2$N | Et | H | ECE | S | nd | 1.05(t, J=8Hz, 3H), 1.30(t, J=7Hz, 3H), 1.57(d, J=5Hz, 3H), 2.37 (quintet, J=8Hz, 1H), 3.20~3.80(m, 2H), 4.20(q, J=7Hz, 2H), 5.01 (d, J=5Hz, 1H), 5.23(brs, 2H), 5.96(dd, J=5Hz, J=9Hz, 1H), 6.33 (s, 1H), 6.42(t, J=8Hz, 1H), 6.53~6.63(m, 1H), 6.80~7.00(m, 1H), | (2-1) |

TABLE 1-continued

Physical constants of pharmaceutical esters $$\text{(I)}$$

| No. | R | R¹ | R² | R³ | X | IR: ν (CHCl₃) cm⁻¹ | NMR: δ (CDCl₃) ppm | Example No |
|---|---|---|---|---|---|---|---|---|
| 10 | H₂N | Et | H | DOL | S | 3480, 3385, 3325 1816, 1781, 1732, 1676, 1523, 1282, 1015. | 1.05(t, J=7.5Hz, 3H), 2.19(s, 3H), 2.38(quintet, J=7.5Hz, 2H), 3.43(dd, A of ABX, J=6.0Hz, 19.8Hz, 1H), 3.70(dd, B of ABX, J=4.0Hz, J=19.8Hz, 1H), 4.95, 5.13(ABq, J=14Hz, 2H), 5.09(d, J=5 Hz, 1H), 5.49(brs, 2H), 6.01(dd, J=5Hz, J=8.5Hz, 1H), 6.30(s, 1H), 6.44(t, J=7.5Hz, 1H), 6.63(dd, X of ABX, J=4Hz, J=6Hz, 1H), 8.35(d, J=8.5Hz, 1H). | (2-1) |
| 11 | H₂N | Et | H | CHAE | S | nd | 0.85~1.90(m, 11H), 1.06(t, J=8Hz, 3H), 1.53(d, J=5Hz, 3H), 2.20 (d, J=6Hz, 2H), 2.38(quintet, J=8Hz, 2H), 3.20~3.76(m, 2H), 5.02 (d, J=5Hz, 1H), 5.25(brs, 2H), 5.96(dd, J=5Hz, J=9Hz, 1H), 6.32 (s, 1H), 6.42(t, J=8Hz, 1H), 6.53~6.63(m, 1H), 6.97(q, J=5Hz, 1H), 8.00, 8.05(2Xd, J=9Hz, 1H). | (2-1) |
| 12 | H₂N | Et | Cl | POM | S | 3470, 3385, 3330, 1783, 1756, 1670, 1602, 1523, 1122, 1103, 985. | 1.05(t, J=7.5Hz, 3H), 1.22(s, 9H), 2.40(quintet, J=7.5Hz, 2H), 3.51, 3.82(ABq, J=18.0Hz, 2H), 5.12(d, J=5.0Hz, 1H), 5.27(bs, 2H), 5.83~6.01(m, 3H), 6.32(s, 1H), 6.41(t, J=7.5Hz, 1H), 8.27 (d, J=8.0Hz, 1H). | (2-1),(5-2) |
| 13 | H₂N | Et | Cl | POM | SO | 3490, 3375, 1805, 1775, 1677, 1601, 1120, 987. | 1.06(t, J=7.5Hz, 3H), 1.22(s, 9H), 2.47(quintet, J=7.5Hz, 2H), 3.65, 3.87(ABq, J=18.0Hz, 2H), 4.66(d, J=5Hz, 1H), 5.47(brs, 2H), 5.86, 5.99(ABq, J=6Hz, 2H), 6.17(dd, J=5Hz, J=10Hz, 1H), 6.38(s, 1H), 6.38(t, J=7.5Hz, 1H), 8.42(d, J=10Hz, 1H). | (2-1) |
| 14 | H₂N | Et | CH₂OCH₃ | POM | S | 3480, 3390, 2960, 1785, 1750, 1670, 1600, 1520, 1360, 1125, 1095. | 1.06(t, J=8Hz, 3H), 1.22(s, 9H), 2.40(quintet, J=8Hz, 2H), 3.32 (s, 3H), 3.56(s, 2H), 4.30(s, 2H), 5.06(d, J=5Hz, 1H), 5.23(brs, 2H), 5.90(s, 2H), 5.95(dd, J=5Hz, J=9Hz, 1H), 6.35(s, 1H), 6.45 (t, J=8Hz, 1H), 8.06(d, J=9Hz, 1H). | (2-1),(2-5) |
| 15 | H₂N | Et | CH₂O—i-Pr | POM | S | 3470, 3370, 2950, 1775, 1740, 1670, 1595, 1360, 1115. | 1.06(t, J=8Hz, 3H), 1.15(d, J=5Hz, 6H), 1.22(s, 9H), 2.37(quintet, J=8Hz, 2H), 3.57(s, 2H), 3.58(septet, J=5Hz, 1H), 4.35(s, 2H), 5.04(d, J=5Hz, 1H), 5.29(brs, 2H), 5.87(s, 2H), 5.92(dd, J=5Hz, J=9Hz, 1H), 6.32(s, 1H), 6.43(t, J=8Hz, 1H), 8.07(d, J=9Hz, 1H). | (2-1) |
| 16 | H₂N | Et | CH₂O(2-propenyl) | POM | S | 3480, 3390, 1785, 1750, 1675, 1600. | 1.03(t, J=7Hz, 3H), 1.20(s, 9H), 2.17~2.52(m, 2H), 3.59(s, 2H), 3.97(m, 2H), 4.38(s, 2H), 5.08(d, J=5Hz, 1H), 5.13~5.36(m, 2H), 5.52(brs, 2H), 5.69~6.11(m, 4H), 6.28(s, 1H), 6.43(t, J=7Hz, 1H), 8.37(d, J=8Hz, 1H). | (2-1) |
| 17 | H₂N | Et | CH₂O(2-fluoroethyl) | POM | S | 3485, 3396, 1785, 1752, 1676, 1602, 1124. | 1.05(t, J=8Hz, 3H), 1.23(s, 9H), 2.38(dq, J=8Hz, 2H), 3.56(s, 2H), 3.66(dt, J=4.5Hz, J=28.8Hz, 2H), 4.40(s, 2H), 4.50 (dt, J=4.5Hz, J=46.8Hz, 2H), 5.03(d, J=5Hz, 1H), 5.19(s, 2H), 5.85(s, 2H), 5.92(dd, J=5Hz, J=8.5Hz, 1H), 6.32(s, 1H), 6.41(t, J=8Hz, 1H), 8.02(d, J=8.5Hz, 1H). | (2-1) |
| 18 | H₂N | Et | CH₂OCOMe | POM | S | 3470, 3380, 1785, 1742, 1670, 1602, 1521, 1122. | 1.05(t, J=8.0Hz, 3H), 1.22(s, 9H), 2.07(s, 3H), 2.88(quintet, J=8.0Hz, 2H), 3.42, 3.61(ABq, J=18.0Hz, 2H), 4.82, 5.12(ABq, J=13.5Hz, 2H), 5.09(d, J=4.5Hz, 1H), 5.45(brs, 2H), 5.86, 5.95 (ABq, J=6.0Hz, 2H), 5.95(dd, J=4.5Hz, J=8.0Hz, 1H), 6.31(s, 1H), 6.44(t, J=8.0Hz, 1H), 8.31(d, J=8.0Hz, 1H). | (2-1) |

7.95(d, J=9Hz, 1H).

TABLE 1-continued

Physical constants of pharmaceutical esters $$\begin{array}{c} \text{structure (I): } N-C(R)=N-S-CH(R^1)-CH=C-CONH-[\beta\text{-lactam}]-CH_2-R^2, COOR^3 \end{array}$$

| No. | R | R¹ | R² | R³ | X | IR: ν (CHCl₃) cm⁻¹ | NMR: δ (CDCl₃) ppm | Example No |
|---|---|---|---|---|---|---|---|---|
| 19 | H₂N | Et | CH₂OCONH₂ | AOE | S | 3480, 3390, 1780, 1727, 1668, 1500, 1325, 1070. | 1.05(t, J=7.5Hz, 3H), 1.53(d, J=6.0Hz, 3H), 2.07(s, 3H), 2.41 (quintet, J=7.5Hz, 2H), 3.38, 3.55(ABq, J=15.0Hz, 2H), 4.78 5.02(ABq, J=13.5Hz, 2/2H), 4.81, 5.05(ABq, J=13.5Hz, 2/2H), 4.99 (s, 2H), 5.01(d, J=5.0Hz, 1H), 5.30(brs, 2H), 5.92(dd, J=5.0Hz, J=9.0Hz, 1H), 6.34(s, 1H), 6.38(t, J=7.5Hz, 1H), 6.96(q, J=6.0 Hz, 1/2H), 7.08(q, J=6.0Hz, 1/2H), 7.94(d, J=9.0Hz, 1/2H), 7.96 (d, J=9.0Hz, 1/2H). | (2-1) |
| 20 | H₂N | Et | CH₂OCONH₂ | POM | S | nd | 1.05(t, J=8.0Hz, 3H), 1.23(s, 9H), 2.38(quintet, J=8.0Hz, 2H), 3.44, 3.68(ABq, J=18.9Hz, 2H), 4.82, 5.08(ABq, J=14.4Hz, 2H), 5.05(d, J=5.0Hz, 2H), 5.14(s, 2H), 5.51(s, 2H), 5.83–6.02(m, 3H), 6.34(s, 1H), 6.41(t, J=8.0Hz, 1H), 8.17(d, J=8.5Hz, 1H). | (2-1) |
| 21 | H₃N⁺—CF₃COO | Et | CH₂OCONH₂ | POM | S | Anal. Calculated for C₂₅H₃₀N₅O₁₀S₂F₃: C, 44.05; H, 4.44; N, 10.28; F, 8.36. Found: C, 44.10, H, 4.62; N, 9.89; F, 8.40. | | (6-1) |
| 22 | H₂N | Et | CH₂OCONH₂ | POE | S | 3480, 3390, 2960, 1785, 1740, 1670, 1390, 1330, 1065. | 1.08(t, J=8Hz, 3H), 1.20(s, 9H), 1.54(d, J=5Hz, 3H), 2.35(quintet, J=8Hz, 2H), 3.44, 3.58(ABq, J=18Hz, 2H), 4.80, 5.02(ABq, J=15Hz, 2H), 5.06(d, J=5Hz, 1H), 5.87, 5.92(2Xd, J=5Hz, 1H), 6.36 (s, 1H), 6.36(t, J=8Hz, 1H), 6.93, 7.02(2Xq, J=5Hz, 1H). [CDCl₃+CD₃OD] | (2-1) |
| 23 | H₂N | Et | CH₂OCONH₂ | ECE | S | nd | 1.06(t, J=7Hz, 3H), 1.30(t, J=7Hz, 3H), 1.56(d, J=6Hz, 3H), 2.35 (quintet, J=7Hz, 2H), 3.50(brs, 2H), 4.22(q, J=7Hz, 2H), 4.82 5.04(ABq, J=15Hz, 2H), 5.03, 5.06(2Xd, J=5Hz, 1H), 5.86, 5.90 (2Xd, J=5Hz, 1H), 6.36(s, 1H), 6.36(t, J=7Hz, 1H), 6.86, 6.97(2Xq, J=6Hz, 1H). [CDCl₃+CD₃OD] | (2-1) |
| 24 | H₂N | Et | CH₂OCONH₂ | DOL | S | 3320br, 1820, 1775, 1726, 1660, 1330, 1077. | 1.07(t, J=8.0Hz, 3H), 2.17(s, 3H), 2.35(quintet, J=8.0Hz, 2H), 3.43, 3.58(ABq, J=18.9Hz, 2H), 4.72, 5.06(ABqmJ=13.5Hz, 2H), 5.01(s, 2H), 5.05(d, J=5Hz, 2H), 5.89(d, J=5Hz, 1H), 6.33(s, 1H), 6.35(t, J=8Hz, 1H). | (2-1), (2-4) |
| 25 | H₂N | Et | CH₂S(1,2,3-thiadiazol-5-yl) | POM | S | 3475, 3390, 2960, 1790, 1750, 1670, 1600, 1360, 1110. | 1.06(t, J=8Hz, 3H), 1.20(s, 9H), 2.43(quintet, J=8Hz, 2H), 3.56 (s, 2H), 4.00, 4.20(ABq, J=13Hz, 2H), 5.04(d, J=5Hz, 1H), 5.36 (brs, 2H), 5.81(s, 2H), 5.91(dd, J=5Hz, J=9Hz, 1H), 6.34(s, 1H), 6.40(t, J=8Hz, 1H), 8.16(d, J=9Hz, 1H), 8.52(s, 1H). | (2-1) |
| 26 | H₂N | Et | CH₂S(1,2,3-thiadiazol-5-yl) | ECE | S | 3436, 3336, 1762, 1663, 1619, 1529, 1373, 1269, 1243, 1074, 995, 867. | 1.06(t, J=7Hz, 3H), 1.32(t, J=7Hz, 3H), 1.54(d, J=6Hz, 3H), 2.42 (quintet, J=7Hz, 2H), 3.54(brs, 2H), 4.06, 4.16(Abq, J=13Hz, 2H),4.23(q, J=7Hz, 2H), 5.01(d, J=5Hz, 1H), 5.46(brs, 2H), 5.90 (dd, J=5Hz, J=8Hz, 1H), 6.33(s, 1H), 6.38(t, J=7Hz, 1H), 6.84(q, J=6Hz, 1H), 8.18(d, J=8Hz, 1H), 8.50(s, 1H). | (2-1) |
| 27 | H₂N | Et | CH₂S(2-Me—1,3,4-thiadiazol-5-yl) | POM | S | 3440, 3340, 3210, 2980, 1785, 1750, 1665, 1620, 1530. [KBr] | 1.03(t, J=8Hz, 3H), 1.20(s, 9H), 2.36(quintet, J=8Hz, 2H), 2.70 (s, 3H), 3.70(s, 2H), 4.17, 4.62(ABq, J=14Hz, 2H), 5.02(d, J=5 Hz, 1H), 5.86, 5.93(ABq, J=5Hz, 2H), 5.90(dd, J=5Hz, J=9Hz, 1H), 6.31(s, 1H), 6.39(t, J=8Hz, 1H), 8.13(d, J=9Hz, 1H). | (2-5) |
| 28 | H₂N | Et | CH₂S(2-H₂N—1,3,4-thiadiazol-5-yl) | POM | S | 3430, 3340, 3190, 2980, 1775, 1745, [KBr] | 1.07(t, J=8Hz, 3H), 1.20(s, 9H), 2.35(quintet, J=8Hz, 2H), 3.65 (brs, 2H), 4.06, 4.23(ABq, J=13Hz, 2H), 5.05(d, J=5Hz, 1H), | (2-5) |

TABLE 1-continued

Physical constants of pharmaceutical esters

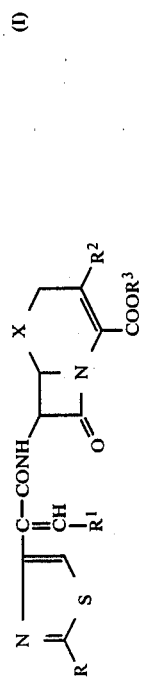

(I)

| No. | R | $R^1$ | $R^2$ | $R^3$ | X | IR: $\nu$ (CHCl$_3$) cm$^{-1}$ | NMR: $\delta$ (CDCl$_3$) ppm | Example No |
|---|---|---|---|---|---|---|---|---|
| 29 | H$_2$N | Et | CH$_2$S(1-HOCH$_2$CH$_2$—tetrazol-5-yl) | POM | S | 1660, 1615, 1520. [KBr] | 5.75~5.92(m, 3H), 6.35(t, J=8Hz, 1H), 6.35(s, 1H) [CDCl$_3$—CD$_3$OD]. | (2-1) |
| 30 | H$_2$N | n-Pr | H | POM | S | 3400, 2970, 1790, 1750, 1675, 1620, 1610, 1530. | 1.07(t, J=8Hz, 3H), 1.23(s, 9H), 2.37(quintet, J=8Hz, 2H), 3.73 (s, 2H), 3.86~4.06(m, 2H), 4.25~4.53(m, 4H), 5.08(d, J=5Hz, 1H), 5.83~5.98(m, 3H), 6.37(s, 1H), 6.37(t, J=8Hz, 1H) [CDCl$_3$—CD$_3$OD]. | (2-1) |
| 31 | H$_2$N | i-Pr | H | POM | S | 3480, 3390, 1780, 1750, 1675, 1640, 1600. | 0.92(t, J=7~8Hz, 3H), 1.21(s, 9H), 1.47(brq, J=7Hz, 2H), 2.30(brq, J=7~8Hz, 2H), 3.23~3.78(m, 2H), 5.05(d, J=5Hz, 1H), 5.60(brs, 2H), 5.82, 5.93(ABq, J=5Hz, 2H), 5.95(dd, J=8Hz, J=5Hz, 1H), 6.37(s, 1H), 6.41(t, J=8Hz, 1H), 6.56~6.65(m, 1H), 8.23(d, J=8 Hz, 1H). | (2-1) |
| 32 | H$_2$N | cyc-Pr | H | POM | S | 3480, 3390, 1740, 1670, 1635, 1600. | 1.06(d, J=7Hz, 6H), 1.22(s, 9H), 2.73~3.13(m, 1H), 3.22~3.77(m, 2H), 5.00(d, J=5Hz, 1H), 5.43(brs, 2H), 5.81, 5.90(ABq, J=5Hz, 2H), 5.96(dd, J=8Hz, J=5Hz, 1H), 6.22(d, J=11Hz, 1H), 6.37(s, 1H), 6.53~6.73(m, 1H), 7.57(d, J=8Hz, 1H). | (2-1) |
| 33 | H$_2$N | t-Bu | H | POM | S | 3480, 3390, 1784, 1745, 1664, 1600, 1122. | 0.5~1.03(m, 4H), 1.20(s, 9H), 2.0~2.5(m, 1H), 3.42(dd, J=7Hz, J=19.8Hz, (A of ABX), 1H), 3.60(dd, J=3Hz, J=19.8Hz, (B of ABX), 1H), 5.03(d, J=5Hz, 1H), 5.30(brs, 2H), 5.80(d, J=11Hz, 1H), 5.84, 5.93(ABq, J=5.4Hz, 2H), 6.03(dd, J=5Hz, J=5Hz, 1H), 6.33 (s, 1H), 6.61(dd, J=3Hz, J=7Hz, (X of ABX), 1H), 8.06(d, J=9Hz, 1H). | (2-1), (2-4) |
| 34 | H$_2$N | cyc-PnMe | H | POM | S | 3480, 3390, 1788, 1745, 1678, 1496, 1123. | 1.18(s, 9H), 1.21(s, 9H), 3.45(dd, A of ABX, J=6.0Hz, J=20.0Hz, 1H), 3.52(dd, B of ABX, J=4.0Hz, J=20.0Hz, 1H), 5.0(d, J=4.5Hz, 1H), 5.18(brs, 2H), 5.80, 5.88(ABq, J=5.5Hz, 2H), 5.98(dd, J=4.5Hz, J=8.5Hz, 1H), 6.33(s, 1H), 6.41(s1H), 6.56(dd, J=4.0Hz, J=6.0Hz, 1H), 6.74(d, J=8.5Hz, 1H). | (2-1) |
| 35 | H$_2$N | cyc-Pn | H | POM | S | 3485, 3390, 1784, 1746, 1672, 1601, 1128. | 0.1~1.3(m, 5H), 1.22(s, 9H), 2.30(dd, J=7.5Hz, 2H), 3.44(dd, J=7Hz, J=19Hz, (A of ABX), 1H), 3.64(dd, J=4Hz, J=19Hz, (B of ABX), 1H), 5.06(d, J=5Hz, 1H), 5.31(brs, 2H), 5.36, 5.46 (ABq, J=5.5Hz, 2H), 6.00(dd, J=5Hz, J=8.5Hz, 1H), 6.38(s, 1H), 6.55(t, J=7.5Hz, 1H), 6.65(dd, J=4Hz, J=7Hz, (X of ABX), 1H), 8.14(d, J=8.5Hz, 1H). | (3-1) |
| 36 | H$_2$N | cyc-PnMe | H | POM | S | 3478, 3385, 1786, 1746, 1670, 1601, 1112. | 1.22(s, 9H), 1.3~2.13(m, 8H), 2.75~3.20(m, 1H), 3.39(dd, J=6.3 Hz, J=19.8Hz, (A of ABX), 1H), 3.58(dd, J=2.7Hz, J=19.8Hz, (B of ABX), 1H), 5.02(d, J=5Hz, 2H), 5.37(brs, 2H), 5.82, 5.94(ABq, J=7Hz, 2H), 6.00(dd, J=5Hz, J=8.5Hz, 1H), 6.35(d, J=10Hz, 1H), 6.38(s, 1H), 6.60(dd, J=2.7Hz, J=8.5Hz, (X of ABX), 1H), 7.96 (d, J=8.5Hz, 1H). | (2-1) |
| | H$_2$N | cyc-PnMe | H | POM | S | 3495, 3395, 1797, 1756, 1678, 1602, 1132. | 1.23(s, 9H), 1.40~1.92(m, 9H), 2.39(dd, J=7.5Hz, 2H), 3.04(dd, J=6.3Hz, J=19Hz, (A of ABX), 1H), 3.62(dd, J=3.6Hz, J=19Hz, (B of ABX), 1H), 5.02(d, J=5.5Hz, 1H), 5.22(brs, 2H), 5.82, 5.92(ABq, J=5.5Hz, 2H), 5.98(dd, J=5.5Hz, J=8.5Hz, 1H), 6.33(s, 1H), 6.45(t, J=7.5Hz, 1H), 6.60(dd, J=3.6Hz, J=6.3Hz, (X of ABX), 1H), 7.85(d, J=8.5Hz, 1H). | (2-1) |

TABLE 1-continued

Physical constants of pharmaceutical esters

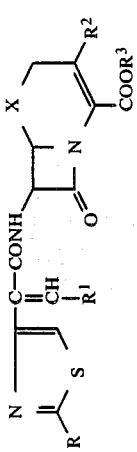
(I)

| No. | R | R¹ | R² | R³ | X | IR: $\nu$ (CHCl₃) cm⁻¹ | NMR: $\delta$ (CDCl₃) ppm | Example No |
|---|---|---|---|---|---|---|---|---|
| 37 | H₂N | cyc-Pn | CH₂OCONH₂ | POM | S | 3480, 3400, 1783, 1740, 1668, 1601, 1122. | 1.21(s, 9H), 1.40~2.0(m, 8H), 2.75~3.12(m, 1H), 3.42, 3.52(ABq, J=19.8Hz, 2H), 4.76, 5.01(ABq, J=14.4Hz, 2H), 4.98(d, J=5Hz, 1H), 5.28(brs, 2H), 5.55(brs, 2H), 5.82, 5.88(ABq, J=6.3Hz, 2H), 5.90(dd, J=5Hz, J=8.5Hz, 1H), 6.28(d, J=9.5Hz, 1H), 6.34(s, 1H), 7.68(d, J=8.5Hz, 1H). | (2-1) |
| 38 | H₂N | MeO—Me | CH₂OCONH₂ | POM | S | 3490, 3431, 3396, 3202, 3189, 1785, 1735, 1668, 1602, 1325, 1123, 1097, 1072, 1000, 982 | 1.22(s, 9H), 3.36(s, 3H), 3.42, 3.59(ABq, J=18Hz, 2H), 4.39(d, J=5.5Hz, 2H), 4.85(brs, 2H), 4.94, 5.23(ABq, J=14Hz, 2H), 5.02 (d, J=4.5Hz, 1H), 5.90(m, 3H), 6.51(s, 1H), 6.56(t, J=5.5Hz, 1H), 8.87(d, J=9Hz, 1H). | (2-1) |

(Abbreviations)
Ac = acetyl, AOE = acetoxyethyl, AOM = acetoxymethyl, BOC = t-butoxycarbonyl, Bu = butyl, Cbz = benzyloxycarbonyl, CHAE = cyclohexylacetoxyethyl, CPBA = chloroperbenzoic acid, cyc- = cyclo-, DCM = dichloromethane, DMA = dimethylacetamide, DMF = dimethylformamide, DOL = 4-methyl-2-oxo-1,3-dioxol-5-ylmethyl, ECE = ethoxycarbonyloxyethyl, Et = ethyl, Me = methyl, nd = not done, POE = pivaloyloxyethyl, POM = pivaloyloxymethyl, Pn = propyl, TFA = trifluoroacetic acid, Yld = yield.

TABLE 2

Physical constants of protected pharmaceutical esters $$\text{(I)}$$

| No | R | R¹ | R² | R³ | X | IR: $\nu$(CHCl₃) cm⁻¹ | NMR: $\delta$(CDCl₃) ppm | Example No |
|---|---|---|---|---|---|---|---|---|
| 1 | BOCNH | Me | H | POM | S | 3415, 3100br; 1786, 1746, 1725, 1678, 1545, 1280, 1155. | 1.20(s, 9H), 1.51(s, 9H), 2.04(d, J=7Hz, 3H), 3.42(dd, A of ABX; J=5Hz, J=9.9Hz, 1H), 3.61(dd, B of ABX, J=3Hz, J=9.9Hz, 1H), 5.02(d, J=5Hz, 1H), 5.85(s, 2H), 5.94(dd, J=5Hz, J=8Hz, 1H), 6.42~6.62(m, 2H), 6.69(s, 1H), 8.01(d, J=8Hz, 1H), 9.62(brs, 1H). | (3-1), (1-3) |
| 2 | BOCNH | Me | CH₂OCONH₂ | POM | S | 3550, 3415, 1787, 1730, 1678, 1545, 1300, 1155. | 1.21(s, 9H), 1.51(s, 9H), 2.02(d, J=7.0Hz, 3H), 3.39, 4.13(ABq, J=17.0Hz, 2H), 4.81, 5.05(ABq, J=13.5Hz, 2H), 5.02(d, J=4.5Hz, 1H), 5.05(s, 2H), 5.87(s, 2H), 5.91(dd, J=4.5Hz, J=8.5Hz, 1H), 6.52(q, J=7.0Hz, 1H), 6.73(s, 1H), 7.90(d, J=8.5Hz, 1H), 8.47 (brs, 1H). | (3-1) |
| 3 | BOCNH | Me | CH₂S(1,2,3-thiadiazol-5-yl) | POM | S | 3420, 2975, 1795, 1755, 1730, 1680, 1550, 1375, 1300, 1160, 1115, 995. | 1.20(s, 9H), 1.50(s, 9H), 2.06(d, J=7Hz, 3H), 3.54(brs, 2H), 3.96, 4.18(ABq, J=13Hz, 2H), 5.03(d, J=5Hz, 1H), 5.80(s, 2H), 5.86(dd, J=5Hz, J=8Hz, 1H), 6.52(q, J=7Hz, 1H), 6.72(s, 1H), 8.15(d, J=8Hz, 1H), 8.52(s, 1H), 9.05(brs, 1H). | (3-1) |
| 4 | BOCNH | Et | H | AOM | S | 3410, 2960, 1785, 1720, 1670, 1540, 1370, 1285, 1155, 1005. | 1.07(t, J=8Hz, 3H), 1.53(s, 9H), 2.10(s, 3H), 2.46(quintet, J=8 Hz, 2H), 3.20~3.76(m, 2H), 4.99(d, J=5Hz, 1H), 5.82, 5.88(ABq, J=6Hz, 2H), 5.95(dd, J=5Hz, J=9Hz, 1H), 6.43(t, J=8Hz, 1H), 6.53~6.63(m, 1H), 6.75(s, 1H), 7.75(d, J=9Hz, 1H), 8.76(brs, 1H). | (3-2) |
| 5 | BOCNH | Et | H | AOE | S | nd | 1.07(t, J=7.5Hz, 3H), 1.53(s, 9H), 1.53(d, J=6.0Hz, 3H), 2.07(s, 3H), 2.48(quintet, J=7.5Hz, 2/2H), 2.50(quintet, J=7.5Hz, 2/2H), 3.21~3.75(m, 2H), 4.94(d, J=4.5Hz, 1/2H), 4.99(d, J=4.5Hz, 1/2H), 5.79~6.02(m, 1H), 6.42(t, J=7.5Hz, 1H), 6.49~6.61(m, 1H), 6.74(s, 1H), 6.93(q, J=6.0Hz, 1/2H), 6.99(q, J=6.0Hz, 1/2H), 7.70(d, J=8.5Hz, 1/2H), 7.74(d, J=8.5Hz, 1/2H), 8.60(brs, 1/2H), 9.55(brs, 1/2H). | (1-2), (3-3) |
| 6 | BOCNH | Et | H | POM | SO | nd | 1.06(t, J=8Hz, 3H), 1.19(s, 9H), 1.52(s, 9H), 2.44(quintet, J=8Hz, 2H), 3.43(dd, A of ABX, J=7Hz, J=19.8Hz, 1H), 3.61(dd, B of ABX, J=4Hz, J=19.8Hz, 1H), 5.03(d, J=5Hz, 1H), 5.83, 5.90 (ABq, J=4.5Hz, 2H), 5.97(dd, J=5Hz, J=8Hz, 1H), 6.45(t, J=8Hz, 1H), 6.58(dd, X of ABX, J=4Hz, J=7Hz, 1H), 6.73(s, 1H), 7.88(d, J=8Hz, 1H), 8.94(brs, 1H). | (3-1), (5-1) |
| 7 | BOCNH | Et | H | POM | S | 3405, 3185br, 1802, 1751, 1720, 1670, 1545, 1155. | 1.08(t, J=7.5Hz, 3H), 1.21(s, 9H), 1.52(s, 9H), 2.52(quintet, J=7.5Hz, 2H), 3.28(dd, A of ABX, J=1.5Hz, J=19.8Hz, 1H), 3.82(dd, B of ABX, J=6.0Hz, 19.8Hz, 1H), 4.59(dd, J=1.5Hz, J=4.5Hz, 1H), 5.84, 5.96(ABq, J=7Hz, 2H), 6.23(dd, J=4.5Hz, J=9Hz, 1H), 6.38 (dd, X of ABX, J=1.5Hz, J=6Hz, 1H), 6.47(t, J=7.5Hz, 1H), 6.72 (s, 1H), 8.81(brs, 1H), 8.94(d, J=9Hz, 1H). | (3-1), (4-1) |
| 8 | BOCNH | Et | H | POE | S | 3410, 1785, 1740, 1726, 1675, 1545, 1290, 1155, 1070. | 1.08(t, J=8Hz, 3H), 1.20(s, 9H), 1.53(s, 9H), 1.53(d, J=5Hz, 3H), 2.25~2.65(m, 2H), 3.20~3.80(m, 2H), 4.97, 5.02(2Xd, J=5Hz, 1H), 5.95(dd, J=5Hz, J=9Hz, 1H), 6.40(t, J=8Hz, 1H), 6.49~6.59 (m, 1H), 6.74(s, 1H), 6.90, 6.96(2Xq, J=7Hz, 1H), 7.40, 7.45(2X d, J=9Hz, 1H). | (3-4) |

TABLE 2-continued
Physical constants of protected pharmaceutical esters $$\text{Structure (I):} \quad R-C(=N-S)-C(=CH-R^1)-CONH-[\beta\text{-lactam with }X]-CH_2-C(R^2)=COOR^3$$

| No | R | R¹ | R² | R³ | X | IR: ν(CHCl₃) cm⁻¹ | NMR: δ(CDCl₃) ppm | Example No |
|---|---|---|---|---|---|---|---|---|
| 9 | BOCNH | Et | H | | ECE | S | 3420, 2960, 1785, 1765, 1730, 1675, 1550, 1370, 1290, 1155, 1080 | 1.07(t, J=7Hz, 3H), 1.30(t, J=7Hz, 3H), 1.53(s, 9H), 1.56(d, J=5 Hz, 3H), 2.30~2.66(m, 2H), 3.10~3.80(m, 2H), 4.20(q, J=7Hz, 2H), 4.94, 5.00(2Xd, J=5Hz, 1H), 5.85, 5.95(2Xdd, J=5Hz, 2H=9Hz, 1H), 6.43(t, J=7Hz, 1H), 6.46~6.63(m, 1H), 6.73(s, 1H), 6.84, 6.90(2X q, J=5Hz, 1H), 7.72(d, J=9Hz, 1H). | (3-5) |
| 10 | BOCNH | Et | H | | DOL | S | 3408, 3220br, 1818, 1783, 1725, 1722, 1670, 1523, 1288, 1153. | 1.07(t, J=7.5Hz, 3H), 1.52(s, 9H), 2.17(s, 3H), 2.96(quintet, J=7.5Hz, 2H), 3.40(dd, A of ABX, J=7.0Hz, J=19.0Hz, 1H), 3.62(dd, B of ABX, J=3.0Hz, J=19.0Hz, 1H), 4.97(s, 2H), 5.00(d, J=5.0 Hz, 1H), 5.94(dd, J=5.0Hz, J=9.0Hz, 1H), 6.43(t, J=7.5Hz, 1H), 6.56(dd, X of ABX, J=3.0Hz, J=7.0Hz, 1H), 6.74(s, 1H), 7.74(d, J=9.0Hz, 1H), 8.72(brs1H). | (3-6) |
| 11 | BOCNH | Et | H | | CHAE | S | 3410, 2930, 1790, 1755, 1730, 1680, 1540, 1290, 1160, 1075. | 0.85~1.95(m, 14H), 1.07(t, J=8Hz, 3H), 1.53(s, 9H), 215~2.65(m, 4H), 3.20~3.80(m, 2H), 4.92, 5.00(2Xd, J=5Hz, 1H), 5.82, 5.95(2X dd, J=5Hz, J=9Hz, 1H), 6.43(t, J=8Hz, 1H), 6.48~6.58(m, 1H), 6.73(s, 1H), 6.92, 6.98(2Xq, J=5Hz, 1H), 7.72, 7.74(2Xd, J=9Hz, 1H). | (3-7) |
| 12 | BOCNH | Et | Cl | | POM | SO | 3395, 3180br, 1802, 1753, 1719, 1668, 1547, 1152, 985. | 1.08(t, J=7.5Hz, 3H), 1.22(s, 9H), 1.52(s, 9H), 2.51(quintet, J=7.5Hz, 2H), 3.64, 3.93(ABq, J=16.2Hz, 2H), 4.76(d, 5.0Hz, 1H), 5.89, 6.00(ABq, J=5.4Hz, 2H), 6.19(dd, J=5.0Hz, J=10.0Hz, 1H), 6.48(t, J=7.5Hz, 1H), 6.73(s, 1H), 8.94(d, J=10.0Hz, 1H), 8.96 (brs, 1H). | (3-1), (4-2) |
| 13 | BOCNH | Et | CH₂OCH₃ | | POM | S | 3420, 2980, 1790, 1750, 1730, 1680, 1550, 1375, 160. | 1.07(t, J=8Hz, 3H), 1.20(s, 9H), 1.53(s, 9H), 2.45(quintet, J=8Hz, 2H), 3.31(s, 3H), 3.53(s, 2H), 4.28(s, 2H), 5.03(d, J=5Hz, 1H), 5.86(s, 2H), 5.90(dd, J=5Hz, J=9Hz, 1H), 6.43(t, J=8Hz, 1H), 6.73(s, 1H), 7.77(d, J=9Hz, 1H), 8.53(brs, 1H). | (3-1) |
| 14 | BOCNH | Et | CH₂O—i-Pr | | POM | S | 3410, 2960, 1780, 1750, 1720, 1670, 1540, 1365, 1150, 1120, 1095 | 1.07(t, J=8Hz, 3H), 1.15(d, J=6Hz, 6H), 1.22(s, 9H), 1.53(s, 9H), 2.46(quintet, J=8Hz, 2H), 3.58(s, 2H), 3.60(septet, J=6Hz, 1H), 4.36(s, 2H), 5.05(d, J=5Hz, 1H), 5.88(s, 2H), 5.90(dd, J=5 Hz, J=9Hz, 1H), 6.45(t, J=8Hz, 1H), 6.75(s, 1H), 7.80(d, J=9Hz, 1H). | (3-1) |
| 15 | BOCNH | Et | CH₂O(2-propenyl) | | POM | S | 3410, 1785, 1750, 1725, 1675. | 1.08(t, J=7Hz, 3H), 1.23(s, 9H), 1.53(s, 9H), 2.27~2.60(m, 2H), 3.58(s, 2H), 3.97(m, 2H), 4.36(s, 2H), 5.04(d, J=5Hz, 2H), 5.13~5.33(m, 2H), 5.67~6.10(m, 4H), 6.41(t, J=7Hz, 1H), 6.73(s, 1H), 7.64(d, J=8Hz, 1H). | (3-1) |
| 16 | BOCNH | Et | CH₂O(2-fluoroethyl) | | POM | S | 3420, 1792, 1755, 1726, 1678, 1548, 1156. | 1.07(t, J=8Hz, 3H), 1.22(s, 9H), 1.52(s, 9H), 2.47(dq, J=8Hz, J=2.5Hz, 2H), 3.68(dt, J=2.5Hz, J=30Hz, 2H), 4.42(s, 2H), 4.54(dt, J=4.5Hz, J=48Hz, 2H), 5.04(d, J=4.5Hz, 1H), 5.87 (s, 2H), 5.94(dd, J=4.5Hz, J=8Hz, 1H), 6.44(t, J=8Hz, 1H), 6.73 (s, 1H), 7.81(d, J=8Hz, 1H), 8.55(brs, 1H). | (3-1) |
| 17 | BOCNH | Et | CH₂OCOMe | | POM | S | 3570br, 3415, 3240br, 1790, 1752, 1730, 1679, | 1.06(t, J=8.0Hz, 3H), 1.21(s, 9H), 1.53(s, 9H), 2.05(s, 3H), 2.44(quintet, J=8.0Hz, 2H), 3.36, 3.55(ABq, J=18.0Hz, 2H), 4.78, 5.07(ABq, J=13.5Hz, 2H), 5.02(d, J=5.0Hz, 1H), 5.86(s, 2H), 5.89 | (1-1), (3-1) |

TABLE 2-continued

Physical constants of protected pharmaceutical esters $$\underset{R}{\overset{N}{\underset{S}{\parallel}}}C-CONH-\underset{\underset{R^1}{CH}}{\overset{\parallel}{C}}-\underset{\underset{O}{\parallel}}{\overset{X}{\underset{}{\vdash}}}\underset{N}{\overset{}{\vdash}}\underset{COOR^3}{\overset{R^2}{\vdash}} \quad (I)$$

| No | R | R¹ | R² | R³ | X | IR: ν(CHCl₃) cm⁻¹ | NMR: δ(CDCl₃) ppm | Example No |
|---|---|---|---|---|---|---|---|---|
| 18 | BOCNH | Et | CH₂OCONH₂ | AOE | S | 1546, 1159. | (dd, J=5.0Hz, J=8.0Hz, 1H), 6.41(t, J=8.0Hz, 1H), 6.71(s, 1H), 7.82(d, J=8.0Hz, 1H), 8.78(brs, 1H). | (3-3) |
| 19 | BOCNH | Et | CH₂OCONH₂ | POM | S | 3520, 3405, 1778, 1722, 1663, 1540, 1149, 1070. | 1.06(t, J=7.5Hz, 3H), 1.46(d, J=6.0Hz, 3H), 1.51(s, 9H), 2.06(s, 3H), 2.45(quintet, J=7.5Hz, 2H), 2.50(quintet, J=7.5Hz, 2/2H), 3.44(brs, 2H), 4.12~5.31(m, 5H), 5.63~5.92(m, 1H), 6.38(t, J=7.5 Hz, 1H), 6.72(s, 1H), 6.89(q, J=6.0Hz, 1/2H), 7.04(q, J=6.0Hz, 1/2H), 7.76(d, J=8.0Hz, 1H). | (1-2), (3-2) |
| 20 | BOCNH | Et | CH₂OCONH₂ | POE | S | nd | 1.07(t, J=7.5Hz, 3H), 1.23(s, 9H), 1.54(s, 9H), 2.47(quintet, J=7.5Hz, 2H), 3.40, 3.56(ABq, J=18.0Hz, 2H), 4.79, 5.07(ABq, J=13.5Hz, 2H), 5.02(d, J=5.0Hz, 1H), 5.03(s, 2H), 5.87(s, 2H), 5.90(dd, J=5.0Hz, J=8.5Hz, 1H), 6.41(t, J=7.5Hz, 1H), 6.76(s, 1H), 7.74(d, J=8.5Hz, 1H), 9.11(s, 1H). | (3-4) |
| 21 | BOCNH | Et | CH₂OCONH₂ | ECE | S | 3500, 3410, 2960, 1775, 1730, 1720, 1670, 1540, 1150, 1070. | 1.07(t, J=8Hz, 3H), 1.20(s, 9H), 1.53(s, 9H), 1.46~1.60(m, 3H), 2.25~2.70(m, 2H), 3.20~3.80(m, 2H), 4.60~5.30(m, 5H), 5.70~6.03 (m, 1H), 6.43(t, J=8Hz, 1H), 6.76(s, 1H), 6.83~7.16(m, 1H), 7.76, 7.81(2Xd, J=9Hz, 1H). | (3-5) |
| 22 | BOCNH | Et | CH₂OCONH₂ | DOL | S | 3520, 3410, 2960, 1780, 1760, 1730, 1720, 1670, 1540, 1370, 1325, 1150, 1075. | 1.08(t, J=8Hz, 3H), 1.32(t, J=7Hz, 3H), 1.55(s, 9H), 1.56(d, J=6 Hz, 3H), 2.42(quintet, J=8Hz, 2H), 3.46, 3.62(ABq, J=20Hz, 2H), 4.23(q, J=7Hz, 2H), 4.86, 5.07(ABq, J=15Hz, 2H), 5.02, 5.08(2Xd, J=5Hz, 1H), 5.53(brs, 2H), 5.87(d, J=5Hz, 1H), 6.43(t, J=8Hz, 1H), 6.77(s, 1H), 6.87, 7.00(q, 2X6Hz, 1H). [CDCl₃ + CD₃OD] | (3-6), (5-3) |
| 23 | BOCNH | Et | CH₂S(1,2,3-thiadiazol-5-yl) | POM | S | 3420, 2980, 1790, 1750, 1730, 1680, 1550, 1375, 1160. | 1.07(t, J=8.0Hz, 3H), 1.20(s, 9H), 1.53(s, 9H), 2.45(quintet, J= 8.0Hz, 2H), 3.31(s, 3H), 3.53(s, 2H), 4.28(s, 2H), 5.03(d, J= 5Hz, 1H), 5.86(s, 2H), 5.90(dd, J=5Hz, J=9Hz, 1H), 6.43(t, J=8 Hz, 1H), 6.73(s, 1H), 7.77(d, J=9Hz, 1H), 8.53(brs, 1H). | (3-1) |
| 24 | BOCNH | Et | CH₂S(1,2,3-thiadiazol-5-yl) | ECE | S | nd | 1.07(t, J=8Hz, 3H), 1.22(s, 9H), 1.52(s, 9H), 2.48(quintet, J=8 Hz, 2H), 3.53(brs, 2H), 4.00, 4.16(ABq, J=15Hz, 2H), 5.02(d, J=5 Hz, 1H), 5.80(s, 2H), 5.86(dd, J=5Hz, J=9Hz, 1H), 6.42(t, J=8Hz, 1H), 6.73(s, 1H), 8.05(d, J=9Hz, 1H), 8.52(s, 1H), 9.22(brs, 1H) | (5-1) |
| 25 | BOCNH | Et | CH₂S(2-Me—1,3,4-thiadiazol-5-yl) | POM | S | 3420, 2975, 1795, 1750, 1730, 1680, 1550, 1375, 1160. | 1.08(t, J=7Hz, 3H), 1.31(t, J=7Hz, 3H), 1.52(s, 9H), 1.53(d, J=6 Hz, 3H), 2.43(quintet, J=7Hz, 2H), 3.62(s, 2H), 4.02, 4.27(ABq, J=13Hz, 2H), 4.25(q, J=7Hz, 2H), 5.09(d, J=5Hz, 1H), 5.86(d, J=5 Hz, 1H), 6.43(t, J=7Hz, 2H), 6.78(s, 1H), 6.85(q, J=6Hz, 1H), 8.56(s, 1H). [CDCl₃ + CD₃OD] | (3-1) |
| 26 | BOCNH | Et | CH₂S(2-H₂N—1,3,4-thiadiazol-5-yl) | POM | S | 3400, 2960, 1780, 1750, 1720, 1670, 1600, 1540, 1370, | 1.07(t, J=8Hz, 3H), 1.20(s, 9H), 2.49(quintet, J=8 Hz, 2H), 2.72(s, 3H), 3.72(s, 2H), 4.24, 4.60(ABq, J=14Hz, 2H), 5.03(d, J=5Hz, 1H), 5.89, 5.96(ABq, J=6Hz, 2H), 5.92(dd, J=5Hz, J=8Hz, 1H), 6.43(t, J=8Hz, 1H), 6.76(s, 1H), 7.82(d, J=8Hz, 1H), 8.53(brs, 1H).<br>1.06(t, J=8Hz, 3H), 1.20(s, 9H), 1.50(s, 9H), 2.49(quintet, J=8 Hz, 2H), 3.64(s, 2H), 4.16(brs, 2H), 5.02(d, J=5Hz, 1H), 5.63 (brs, 2H), 5.83, 5.90(ABq, J=6Hz, 2H), 5.90(dd, J=5Hz, J=9Hz, | (3-1) |

TABLE 2-continued

Physical constants of protected pharmaceutical esters $$\underset{R}{\overset{N}{\underset{S}{\parallel}}}C-CONH\underset{\overset{|}{CH}}{\underset{\overset{|}{R^1}}{\parallel}}\begin{array}{c}\phantom{0}\\\phantom{0}\\\phantom{0}\end{array}\underset{O}{\overset{X}{\underset{N}{\overline{\phantom{XX}}}}}\begin{array}{c}R^2\\\overline{\phantom{XX}}\\COOR^3\end{array}\quad (I)$$

| No | R | R¹ | R² | R³ | X | IR: ν(CHCl₃) cm⁻¹ | NMR: δ(CDCl₃) ppm | Example No |
|----|---|----|----|----|---|-------------------|-------------------|------------|
| 27 | BOCNH | Et | CH₂S(1-HOCH₂CH₂—tetrazol-5-yl) | POM | S | 3420, 2980, 1790, 1750, 1730, 1675, 1540, 1375, 1160, 1150. | 1H), 6.40(t, J=8Hz, 1H), 6.75(s, 1H), 8.06(d, J=9Hz, 1H), 9.25 (brs, 1H). 1.06(t, J=8Hz, 3H), 1.20(s, 9H), 1.50(s, 9H), 2.50(quintet, J=8 Hz, 2H), 3.70(s, 2H), 3.95~4.15(m, 2H), 4.20~4.45(m, 4H), 5.03 (d, J=5Hz, 1H), 5.88(s, 2H), 5.86(dd, J=9Hz, J=5Hz, 1H), 6.40 (t, J=8Hz, 1H), 6.77(s, 1H), 7.95(d, J=9Hz, 1H), 9.00(brs, 1H). | (3-1) |
| 28 | BOCNH | n-Pr | H | POM | S | 3500, 3400, 3200, 1785, 1750, 1720, 1665, 1640. | 0.96(t, J=7Hz, 3H), 1.22(s, 9H), 1.53(s, 9H), 1.40~1.63(m, 2H), 2.40(brq, J=7Hz, 2H), 3.23~3.77(m, 2H), 5.02(d, J=5Hz, 1H), 5.82, 5.90(ABq, J=6Hz, 2H), 5.97(dd, J=8Hz, J=5Hz, 1H), 6.43(t, J=8Hz, 1H), 6.52~6.63(m, 1H), 6.75(s, 1H), 7.50(d, J=8Hz, 1H). | (3-1) |
| 29 | BOCNH | i-Pr | H | POM | S | 3500, 3400, 3220, 1785, 1745, 1720, 1675, 1635. | 1.07(d, J=7Hz, 6H), 1.20(s, 9H), 1.53(s, 9H), 2.71~3.18(m, 1H), 3.27~3.80(m, 2H), 5.03(d, J=5Hz, 1H), 5.83, 5.92(ABq, J=5Hz, 2H), 5.97(dd, J=8Hz, J=5Hz, 1H), 6.30(d, J=11Hz, 1H), 6.53~6.65 (m, 1H), 6.79(s, 1H), 7.67(d, J=8Hz, 1H), 8.33(brs, 2H). | (3-1) |
| 30 | BOCNH | cyc-Pr | H | POM | S | 3415, 1788, 1750, 1726, 1670, 1545, 1157. | 0.5~1.02(m, 4H), 1.22(s, 9H), 1.53(s, 9H), 2.10~2.45(m, 1H), 3.42(dd, J=5.4Hz, J=18Hz, (A of ABX), 1H), 3.61(dd, J=2.7Hz, J= 18Hz, (B of ABX), 1H), 5.02(d, J=5Hz, 1H), 5.78(d, J=12Hz, 1H), 5.80, 5.89(ABq, J=5Hz, 2H), 5.99(dd, J=5Hz, J=8.5Hz, 1H), 6.55 (dd, J=2.7Hz, J=5.4Hz, (X of ABX), 1H), 7.79(d, J=8.5Hz, 1H). | (3-1) |
| 31 | BOCNH | cyc-PrMe | H | POM | S | nd | 0.03~1.3(m, 5H), 1.20(s, 9H), 1.51(s, 9H), 2.34(dd, J=7.5Hz, J= 7.5Hz, 2H), 3.39(dd, J=5.5Hz, J=19.8Hz, (A of ABX), 1H), 3.57 (dd, J=3.6Hz, J=19.8Hz, (B of ABX), 1H), 4.98(d, J=5Hz, 1H), 5.80, 5.87(ABq, J=4.5Hz, 2H), 5.91(dd, J=5Hz, J=8.5Hz, 1H), 6.52 (t, J=7.5Hz, 1H), 6.53(dd, J=3.6Hz, J=5.5Hz, (X of ABX), 1H), 6.75(s, 1H), 7.76(d, J=8.5Hz, 1H), 8.70(brs, 1H). | (3-1) |
| 32 | BOCNH | t-Bu | H | POM | S | 3415, 1793, 1750, 1726, 1682, 1545, 1157, 1003. | 1.17(s, 9H), 1.21(s, 9H), 1.52(s, 9H), 3.38(dd, A of ABX, J=6.0 Hz, J=18.5Hz, 1H), 3.57(dd, B of ABX, J=3.0Hz, J=18.5Hz, 1H), 5.0(d, J=5.0Hz, 1H), 5.81, 5.90(ABq, J=5.5Hz, 2H), 6.0(dd, J= 5.0Hz, J=9.0Hz, 1H), 6.41(s, 1H), 6.56(dd, X of ABX, J=3.0Hz, J=6.0Hz, 1H), 6.70(d, J=9.0Hz, 1H), 8.83(brs, 1H). | (3-1) |
| 33 | BOCNH | cyc-Pn | CH₂OCONH₂ | POM | S | 3520, 3410, 1782, 1740, 1724, 1670, 1539, 1150. | 1.22(s, 9H), 1.53(s, 9H), 1.30~2.0(m, 8H), 2.85~3.16(m, 1H), 3.44(ABq, J=18.5Hz, 2H), 4.81, 5.07(ABq, J=13.5Hz, 2H), 5.04(d, J=5Hz, 2H), 5.28(brs, 1H), 5.87, 5.94(ABq, J=5.8Hz, 2H), 5.92 (dd, J=5Hz, J=7.5Hz, 1H), 6.35(d, J=10Hz, 1H), 6.77(s, 1H), 7.64 (d, J=7.5Hz, 1H). | (3-1) |
| 34 | BOCNH | cyc-PnMe | H | POM | S | 3415, 1787, 1750, 1723, 1674, 1542, 1155. | 1.21(s, 9H), 1.30~1.88(m, 9H), 1.52(s, 9H), 2.48(dd, J=8Hz, 2H), 3.42(dd, J=6Hz, J=19Hz, (A of ABX), 1H), 3.61(dd, J=3.6Hz, J=19 Hz, (B of ABX), 1H), 5.03(d, J=4.5Hz, 1H), 5.84, 5.92(ABq, J=4.5 Hz, 2H), 5.96(dd, J=4.5Hz, J=8.5Hz, 1H), 6.49(t, J=8Hz, 1H), 6.60(dd, J=3.6Hz, J=6Hz, (X of ABX), 1H), 6.77(s, 1H), 7.64(d, J=8.5Hz, 1H), 8.48(brs, 1H). | (3-1) |
| 35 | BOCNH | MeO—Me | CH₂OCONH₂ | POM | S | 3517, 3418, 3183, | 1.23(s, 9H), 1.52(s, 9H), 3.37(s, 3H), 3.35, 3.57(ABq, J=18Hz, | (3-1) |

TABLE 2-continued

Physical constants of protected pharmaceutical esters $$\text{(I)}$$

| No | R | R¹ | R² | R³ | X | IR: ν(CHCl₃) cm⁻¹ | NMR: δ(CDCl₃) ppm | Example No |
|---|---|---|---|---|---|---|---|---|
| | | | | | | 1784, 1728, 1676, 1622, 1327, 1298, 1154, 1121, 1093, 1072, 999, 981. | 2H), 4.43(d, J=5.5Hz, 2H), 4.77, 5.04(ABq, J=14Hz, 2H), 4.98(d, J=4.5Hz, 1H), 5.10(brs, 2H), 5.78(dd, J=4.5Hz, J=8Hz, 1H), 5.85 (s, 2H), 6.57(t, J=5.5Hz, 1H), x6.92(s, 1H), 8.34(d, J=8Hz, 1H). | (3-1) |
| 36 | CbzNH | Et | H | POM | S | 3410, 3240br, 1790, 1750, 1738, 1678, 1552, 1290, 1130, 1095. | 1.03(t, J=7.5Hz, 3H), 1.20(s, 9H), 2.38(quintet, J=7.5Hz, 2H), 3.30(dd, A of ABX, J=6Hz, J=18.9Hz, 1H), 3.51(dd, B of ABX, J=3 Hz, J=18.9Hz, 1H), 4.98(d, J=5.5Hz, 1H), 5.15, 5.30(ABq, J=13.0 Hz, 2H), 5.78, 5.85(Abq, J=4.5Hz, 2H), 5.92(dd, J=5.5Hz, J=8Hz, 1H), 6.43(t, J=7.5Hz, 1H), 6.70(s, 1H), 7.36(s, 5H), 7.89(d, J=8 Hz, 1H), 9.45(brs, 1H). | (7-1) |
| 37 | OHCNH | Et | H | POM | S | 2970, 1790, 1755, 1705, 1680, 1550, 1290, 1130. | 1.07(t, J=8Hz, 3H), 1.20(s, 9H), 2.37(quintet, J=8Hz, 2H), 3.20~ 3.76(m, 2H), 4.97(d, J=5Hz, 1H), 5.82(s, 2H), 5.92(dd, J=5Hz, J= 9Hz, 1H), 6.45(t, J=8Hz, 1H), 6.50~6.62(m, 1H), 6.77(s, 1H), 7.93(d, J=9Hz, 1H), 8.49(s, 1H). | (7-1) |
| 38 | ClCH₂CONH | Et | H | POM | S | 3500, 3370, 3230, 1790, 1755, 1685, 1640. | 1.08(t, J=8Hz, 3H), 1.22(s, 9H), 2.25~2.63(m, 2H), 3.23~3.78(m, 2H), 4.27(s, 2H), 5.02(d, J=5Hz, 1H), 5.86(s, 2H), 5.90(dd, J=5Hz, J=5Hz, 1H), 6.47(t, J=9Hz, 1H), 6.55~6.61(m, 1H), 6.85(s, 1H), 7.78(d, J=8Hz, 1H). | (7-1) |
| 39 | NO₂PhCHN— | Et | H | POM | S | 3410, 1785, 1745, 1675, 1635, 1520, 1345. | 1.14(t, J=7Hz, 3H), 1.22(s, 9H), 2.56(q, J=7Hz, 2H), 3.23~3.82 (m, 2H), 5.08(d, J=5Hz, 1H), 5.87, 5.97(ABq, J=5Hz, 2H), 6.03 (dd, J=5Hz, J=8Hz, 1H), 6.57~6.69(m, 1H), 6.69(t, J=7Hz, 1H), 7.27(s, 1H), 7.71(d, J=8Hz, 1H), 8.16, 8.34(ABq, J=9Hz, 4H), 9.21(s, 1H). | (7-1) |

TABLE 3

Synthesis of Pharmaceutical esters

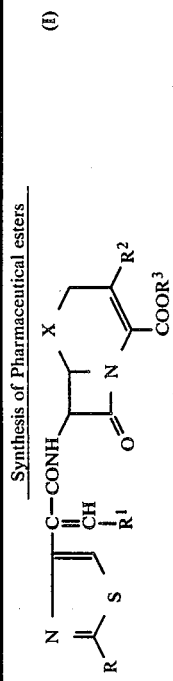

(I)

| No. | R | R¹ | R² | R³ | Ex. No. | Start. Mat. (mg) | X | Solvent (ml) | Reagent | Subreagent | Time (hr) | Temp (°C.) | Yld. (%) | Crop (mg) |
|---|---|---|---|---|---|---|---|---|---|---|---|---|---|---|
| 1 | H₂N | Me | H | POM | (2-1) | R = BOCNH 100 | S | — | TFA 1 ml | anisole 0.5 ml | 1 | rt | 85 | 70 |
| 2 | H₂N | Me | CH₂OCONH₂ | POM | (2-4) | R = BOCNH 150 | S | DCM 1 | AlCl₃ 51 mg 1.5 eq. | | 0.1 | −30 | 74 | 92 |
| 3 | H₂N | Me | CH₂S(1,2,3-thiadiazol-5-yl) | POM | (2-5) | R = BOCNH 160 | S | — | TFA 2 ml | | 2 | rt | 55 | 75 |
| 4 | H₂N | Et | H | AOM | (2-1) | R = BOCNH 102 | S | — | TFA 2 ml | | 0.8 | rt | 55 | 48 |
| 5 | H₂N | Et | H | AOE | (2-1) | R = BOCNH 163 | S | — | TFA 3 ml | | 1 | rt | 87 | 116 |
|  |  |  |  |  | (3-3) | R³ = H 95 | S | DMF 1 | TFA 1.5 ml | | 1 | rt | 59 | 45 |
| 6 | H₂N | Et | H | POM | (2-1) | R = BOCNH 480 | S | — | AOEBr 165 μl | K₂CO₃ 110 mg | 2.5 | −30~0 | 33 | 38 |
|  |  |  |  |  | (2-2) | R = ClCH₂CONH 143 | S | THF 2 | TFA 5 ml | AcONa 41 mg 2 eq. MeOH 2 ml | 1 | rt | 87 | 340 |
|  |  |  |  |  |  |  |  |  | NH₂CSNH₂ 76 mg 4 eq |  | 4 | rt | 80 | 99 |
|  |  |  |  |  | (2-3) | R = HCONH 183 | S | HOAc 2 | N—HCl 0.3 ml | anisole 0.5 ml | 3.5 | rt | 63 | 110 |
|  |  |  |  |  | (2-4) | R = BOCNH 120 | S | DCM 1 | AlCl₃ 80 mg 3 eq | | 0.1 | −30 | 81 | 80 |
|  |  |  |  |  | (3-1) | R³ = H 114 | S | DMF 1.5 | POM 56 μl 1.1 eq | K₂CO₃ 62 mg 2 eq | 0.5 | −30 | 33 | 49 |
|  |  |  |  |  | (5-2) | X = SO 100 | S | DCM 4 | PBr₃ 40 μl 2 eq | | 0.8 | −30 | 66 | 78 |
| 7 | H₂N HCl | Et | H | POM | (6-2) | R = NH₂ 82 | S | DCM 1 | HCl/EtOAc | then rinsed with Et₂O | — | — | 87 | 63 |
| 8 | H₂N | Et | H | POE | (2-1) | R = BOCNH 160 | S | — | TFA 3 ml | | 1 | rt | 47 | 63 |
| 9 | H₂N | Et | H | ECE | (2-1) | R = BOCNH 189 | S | — | TFA 3.5 ml | | 1 | rt | 76 | 119 |
| 10 | H₂N | Et | H | DOL | (2-1) | R = BOCNH 83 | S | — | TFA 1 ml | | 1.5 | rt | 62 | 43 |
| 11 | H₂N | Et | H | CHAE | (2-1) | R = BOCNH 150 | S | — | TFA 3 ml | | 1 | rt | 69 | 88 |
| 12 | H₂N | Et | Cl | POM | (2-1) | R = BOCNH 130 | S | — | TFA 1.5 ml | | 2 | rt | 64 | 70 |
| 13 | H₂N | Et | Cl | POM | (5-2) | X = SO 51 | SO | DCM 2 | PBr₃ 19 μl | | 1 | −30 | 83 | 41 |
| 14 | H₂N | Et | CH₂OCH₃ | POM | (2-1) | R = BOCNH 130 | S | — | TFA 1 ml | | 2.5 | rt | 25 | 28 |
| 15 | H₂N | Et | CH₂O-i-Pr | POM | (2-1) | R = BOCNH 173 | S | — | TFA 3.5 ml | | 1 | rt | 90 | 131 |
| 16 | H₂N | Et | CH₂O(2-propenyl) | POM | (2-5) | R = BOCNH 173 | S | DCM 1.5 | AlCl₃ 72 mg 2 eq | anisole 1 | 0.2 | −30 | 86 | 125 |
| 17 | H₂N | Et | CH₂O(2-fluoroethyl) | POM | (2-1) | R = BOCNH 150 | S | — | TFA 3 ml | | 1 | rt | 33 | 42 |
| 18 | H₂N | Et | CH₂OCOMe | POM | (2-1) | R = BOCNH 128 | S | — | TFA 1 ml | anisole 0.3 ml | 1 | rt | 47 | 80 |
| 19 | H₂N | Et | CH₂OCONH₂ | AOE | (2-1) | R = BOCNH 150 | S | DCM 0.7 | TFA 0.33 ml | anisole 0.25 ml | 2.5 | rt | 87 | 110 |
| 20 | H₂N | Et | CH₂OCONH₂ | POM | (2-1) | R = BOCNH 80 | S | — | TFA 1 ml | | 2 | rt | 52 | 54 |
| 21 | H₃N⁺—CF₃COO | Et | CH₂OCONH₂ | POM | (2-1) | R = BOCNH 450 | S | — | TFA 0.6 ml | | 1 | rt | 64 | 43 |
| 22 | H₂N | Et | CH₂OCONH₂ | POM | (6-1) | R = NH₂ 290 | S | DCM 4 | TFA 5 ml | | 2 | rt | 76 | 290 |
| 23 | H₂N | Et | CH₂OCONH₂ | POE | (2-1) | R = BOCNH 102 | S | — | TFA 1 | then rinsed with Et₂O | — | — | 83 | 290 |
| 24 | H₂N | Et | CH₂OCONH₂ | ECE | (2-1) | R = BOCNH 165 | S | — | TFA 2 ml | | 0.8 | −30 | 48 | 42 |
|  | H₂N | Et | CH₂OCONH₂ | DOL | (2-1) | R = BOCNH 110 | S | — | TFA 3.5 ml | | 1 | rt | 50 | 70 |
|  | H₂N | Et | CH₂S(1,2,3-thiadiazol-5-yl) | POM | (2-4) | R = BOCNH 110 | S | DCM 1 | TiCl₄ 38 μl 2 eq | anisole 1 ml | 2.5 | rt | 27 | 25 |
| 25 | H₂N | Et | CH₂S(1,2,3-thiadiazol-5-yl) | POM | (2-1) | R = BOCNH 105 | S | — | TFA 2 ml | | 0.3 | −30 | 74 | 69 |
| 26 | H₂N | Et | CH₂S(1,2,3-thiadiazol-5-yl) | ECE | (2-1) | R = BOCNH 105 | S | — | TFA 2 ml | | 7/6 | rt | 92 | 84 |
| 27 | H₂N | Et | CH₂S(2-Me—1,3,4-thiadiazol-5-yl) | POM | (2-1) | R = BOCNH 186 | S | — | TFA 3.7 ml | | 0.7 | rt | 43 | 39 |
| 28 | H₂N | Et | CH₂S(2-H₂N—1,3,4-thiadiazol-5-yl) | POM | (2-1) | R = BOCNH 128 | S | — | TFA 2.5 ml | | 11/6 | rt | 85 | 136 |
| 29 | H₂N | Et | CH₂S(1- | POM | (2-1) | R = BOCNH 181 | S | — | TFA 3.7 ml | | 2 | rt | 88 | 98 |
|  |  |  |  |  |  |  |  |  |  |  | 2 | rt | 60 | 94 |

TABLE 3-continued

Synthesis of Pharmaceutical esters

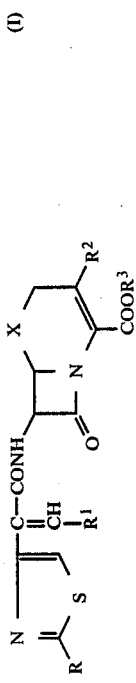
(I)

| No. | R | R¹ | R² | R³ | X | Ex. No. | Start. Mat. (mg) | Solvent (ml) | Reagent | Subreagent | Time (hr) | Temp (°C.) | Yld. (%) | Crop (mg) |
|---|---|---|---|---|---|---|---|---|---|---|---|---|---|---|
| 30 | H₂N | n-Pr | HOCH₂CH₂—tetrazol-5-yl) H | POM | S | (2-1) | R = BOCNH 201 | — | TFA 1 ml | | 3 | rt | 60 | 100 |
| 31 | H₂N | i-Pr | H | POM | S | (2-1) | R = BOCNH 186 | — | TFA 1 ml | | 3 | rt | 70 | 108 |
| 32 | H₂N | cyc-Pr | H | POM | S | (2-1) | R = BOCNH 133 | — | TFA 2.6 ml | | 1 | rt | 59 | 65 |
| 33 | H₂N | t-Bu | H | POM | S | (2-1) | R = BOCNH 53 | — | TFA 1 ml | | 2 | rt | 90 | 40 |
| | | | | | | (2-4) | R = BOCNH 106 | DCM 1 | SnCl₄ 40 μl 2 eq | anisole 1 | 1 | −10 | 85 | 75 |
| 34 | H₂N | cyc-PrMe | H | POM | S | (2-1) | R = BOCNH 64 | — | TFA 1 ml | | 2 | rt | 65 | 35 |
| 35 | H₂N | cyc-Pn | H | POM | S | (3-1) | R³ = H 102 | DMF 2 | POM I 50 μl 1.2 eq | K₂CO₃ 67 mg | 1 | −25 | 53 | 69 |
| 36 | H₂N | cyc-PnMe | H | POM | S | (2-1) | R = BOCNH 105 | — | TFA 2 ml | | 0.7 | rt | 91 | 80 |
| 37 | H₂N | cyc-Pn | CH₂OCONH₂ | POM | S | (2-1) | R = BOCNH 210 | — | TFA 2 ml | | 2.5 | rt | 76 | 127 |
| 38 | H₂N | MeO—Me | CH₂OCONH₂ | POM | S | (2-1) | R = BOCNH 198 | DCM 2 | TFA 500 μl | | 6.3 | rt | 62 | 108 |

TABLE 4

Synthesis of protected pharmaceutical esters

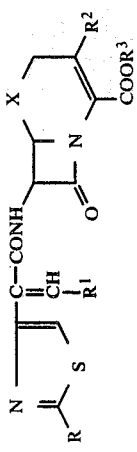

(I)

| No. | R | R¹ | R² | R³ | X | Ex. No. | Start. Mat. (mg) | Solvent (ml) | Reagent | Subreagent | Time (hr) | Temp (°C) | Yld. (%) | Crop (mg) |
|---|---|---|---|---|---|---|---|---|---|---|---|---|---|---|
| 1 | BOCNH | Me | H | POM | S | (3-1) | R³ = H 100 | DMF 1 | POMI 45 μl | K₂CO₃ 45 mg | 0.5 | −30 | 80 | 100 |
|  |  |  |  |  |  | (1-3) | H₂NQ" 157 | DCM 10 | Q'COOH 142 mg, (COCl)₂ 42.6 μl 1 eq | picoline 98 μl 2 eq | 0.5 | −40 | 56 | 162 |
| 2 | BOCNH | Me | CH₂OCONH₂ | POM | S | (3-1) | R³ = H 216 | DMF 4 | POMI 78 μl | K₂CO₃ 110 mg | 0.7 | −20 | 57 | 150 |
| 3 | BOCNH | Me | CH₂S(1,2,3-thiadiazol-5-yl) | POM | S | (3-1) | R³ = H 234 | DMF 2.3 | POMI 100 μl | K₂CO₃ 152 mg | 0.5 | −25∼−30 | 37 | 104 |
| 4 | BOCNH | Et | H | AOM | S | (3-2) | R³ = H 240 | DMF 2.4 | AOMBr 115 mg | K₂CO₃ 138 mg | 0.7 | 0 | 48 | 132 |
| 5 | BOCNH | Et | H | AOE | S | (1-4) | H₂NQ" 161 | DCM 8 | Q'COOH 149 mg, MeSO₂Cl 40 μl | NEt₃ 83 μl Me—morpholine 132 μl | 3 | −60 | 83 | 235 |
| 6 | BOCNH | Et | H | POM | S | (3-3) | R³ = H 170 | DMF 2 | AOEBr 230 μl | K₂CO₃ 152 mg | 1.5 | −20 | 32 | 65 |
|  | BOCNH | Et | H | POM | S | (3-1) | R³ = H 572 | DMF 8 | POMI 223 μl | K₂CO₃ 329 mg | 1 | −30 | 68 | 485 |
| 7 | BOCNH | Et | H | POM | SO | (5-1) | X = SO 61 | DCM 2 | PBr₃ 19.3 μl 2 eq |  | 0.5 | −30 | 86 | 51 |
|  | BOCNH | Et | H | POM | SO | (3-1) | R³ = H 175 | DMF 3.5 | POMI 68 μl | K₂CO₃ 97.5 mg | 2 | −20 | 48 | 103 |
|  | BOCNH | Et | H | POM | S | (4-1) | X = S 300 | DCM 8 | m-CPBA 108 mg |  | 0.25 | rt | 90 | 275 |
| 8 | BOCNH | Et | H | POE | S | (3-4) | R³ = H 240 | DMF 2.4 | POEI 460 μl, POECl 320 μl | K₂CO₃ 138 mg | 1 | −25∼−30 | 53 | 161 |
| 9 | BOCNH | Et | H | ECE | S | (3-5) | R³ = H 240 | DMF 2.4 | ECEBr 150 mg 1.5 eq | K₂CO₃ 138 mg | 0.5 | −10 | 64 | 191 |
| 10 | BOCNH | Et | H | DOL | S | (3-6) | R³ = H 240 | DMF 4 | DOLBr 102 mg 1.5 eq | K₂CO₃ 83 mg | 0.5 | 0 | 47 | 83 |
| 11 | BOCNH | Et | H | CHAE | S | (3-7) | R³ = H 240 | DMF 2.4 | CHAEI 355 mg | K₂CO₃ 138 mg | 0.8 | −30 | 47 | 152 |
| 12 | BOCNH | Et | Cl | POM | S | (3-1) | R³ = H 106 | DMF 3 | POMI 38 μl 1.1 eq | K₂CO₃ 55 mg | 0.7 | −30 | 58 | 75 |
|  |  |  |  |  | SO | (4-2) | X = S 410 | DCM 4 | m-CPBA 47.4 mg |  | 0.3 | 0 | 30 | 135 |
| 13 | BOCNH | Et | CH₂OCH₃ | POM | S | (3-1) | R³ = H 159 | DMF 1.5 | POMI 77 μl | K₂CO₃ 84 mg | 1 | −30 | 90 | 173 |
| 14 | BOCNH | Et | CH₂O—i-Pr | POM | S | (3-1) | R³ = H 120 | DMF 1.2 | POMI 55 μl | K₂CO₃ 152 mg | 1 | −30 | 97 | 140 |
| 15 | BOCNH | Et | CH₂O(2-propenyl) | POM | S | (3-1) | R³ = H 193 | DMF 2 | POMI 120 μl 2 eq | K₂CO₃ 97 mg | 2 | −40 | 55 | 128 |
| 16 | BOCNH | Et | CH₂O(2-fluoroethyl) | POM | S | (3-1) | R³ = H 175 | DMF 2 | POMI 64 μl 1.2 eq | K₂CO₃ 87 mg | 0.5 | −35 | 81 | 170 |
| 17 | BOCNH | Et | CH₂OCOMe | POM | S | (1-1) | H₂NQ" 193 | DCM 2 | Q'COOH 164 mg 1.1 eq, cyanuric Cl 194 mg 1.1 eq | pyridine 162 μl 4 eq | 1.5 | −15 | 48 | 160 |
| 18 | BOCNH | Et | CH₂OCONH₂ | AOE | S | (3-1) | R³ = H 123 | DMF 2 | POMI 43 μl | K₂CO₃ 62 mg | 1 | −30 | 84 | 123 |
| 19 | BOCNH | Et | CH₂OCONH₂ | POM | S | (3-3) | R³ = H 166 | DMF 3 | AOEBr 43 μl 1.2 eq | K₂CO₃ 83 mg | 3 | 0 | 36 | 70 |
|  |  |  |  |  |  | (1-2) | H₂NQ" 194 | DCM 1 | Q'COOH 149 mg 1 eq | NEt₃ 125 μl, POCl₃ 52 μl | 1 | −5 | 54 | 180 |
| 20 | BOCNH | Et | CH₂OCONH₂ | POE | S | (3-4) | R³ = H 186 | DMF 8 | POMI 220 μl | K₂CO₃ 318 mg | 1.5 | −30 | 74 | 570 |
| 21 | BOCNH | Et | CH₂OCONH₂ | ECE | S | (3-5) | R³ = H 254 | DMF 2.5 | POMI 120 μl | K₂CO₃ 91 mg | 2 | −10∼−30 | 45 | 104 |
| 22 | BOCNH | Et | CH₂OCONH₂ | DOL | S | (5-3) | X = SO 160 | DCM 15 | ECEBr 272 mg | K₂CO₃ 127 mg | 1.5 | 0 | 54 | 166 |
|  |  |  |  |  |  | (3-6) | R³ = H 123 | DMF 3 | PBr₃ 65 μl 3 eq | K₂CO₃ 61 mg | 0.7 | −30 | 72 | 110 |
| 23 | BOCNH | Et | CH₂S(1,2,3-thiadiazol-5-yl) | POM | S | (3-1) | R³ = H 310 | DMF 3 | DOLBr 75 mg 1.5 eq | K₂CO₃ 140 mg | 5/6 | 0 | 64 | 94 |
| 24 | BOCNH | Et | CH₂S(1,2,3-thiadiazol-5-yl) | ECE | S | (5-1) | X = SO 170 | DCM 4 | POMI 130 μl |  | 0.5 | −25 | 29 | 107 |
| 25 | BOCNH | Et | CH₂S(2-Me—1,3,4-thiadiazol-5-yl) | POM | S | (3-1) | R³ = H 279 | DMF 5 | PBr₃ 55 μl 2 eq | K₂CO₃ 93 mg | 1 | −25 | 63 | 105 |
|  |  |  |  |  |  |  |  |  | POMI 150 μl |  |  | −25∼−30 | 56 | 186 |
| 26 | BOCNH | Et | CH₂S(1-HOCH₂CH₂N—1,3,4-thiadiazol-5-yl) | POM | S | 3-1) | R³ = H 195 | DMF 3 | POMI 63 μl | K₂CO₃ 86 mg | 1 | −15∼−30 | 55 | 128 |
| 27 | BOCNH | Et | CH₂S(1-HOCH₂CH₂—tetrazol-5-yl) | POM | S | (3-1) | R³ = H 279 | DMF 3 | POMI 112 μl | K₂CO₃ 122 mg | 1 | −15∼−30 | 55 | 183 |
| 28 | BOCNH | n-Pr | H | POM | S | (3-1) | R³ = H 289 | DMF 4 | POMI 200 μl | K₂CO₃ 163 mg | 1 | −20 | 70 | 201 |

TABLE 4-continued

Synthesis of protected pharmaceutical esters $$\text{R-}\underset{S}{\overset{N}{\bigvee}}\text{-CH=CH-CONH-}\underset{O}{\overset{\phantom{x}}{\underset{\phantom{x}}{\bigsqcap}}}\underset{\phantom{x}}{\overset{X}{\bigvee}}\text{-CH}_2\text{-C(R}^2\text{)=C(COOR}^3\text{)} \quad (I)$$

| No. | R | R¹ | R² | R³ | X | Ex. No. | Start. Mat. (mg) | Solvent (ml) | Reagent | Subreagent | Time (hr) | Temp (°C) | Yld. (%) | Crop (mg) |
|---|---|---|---|---|---|---|---|---|---|---|---|---|---|---|
| 29 | BOCNH | i-Pr | H | POM | s | (3-1) | R³ = H 259 | DMF 4 | POMI 170 μl | K₂CO₃ 138 mg | 2/3 | −30 | 63 | 186 |
| 30 | BOCNH | cyc-Pr | H | POM | s | (3-1) | R³ = H 312 | DMF 3 | POMI 118 μl 1.2 eq | K₂CO₃ 128 mg | 1.5 | −30 | 47 | 133 |
| 31 | BOCNH | cyc-PrMe | H | POM | s | (3-1) | R³ = H 150 | DMF 2 | POMI 61 μl 1.2 eq | K₂CO₃ 60 mg | 0.5 | −30 | 34 | 64 |
| 32 | BOCNH | t-Bu | H | POM | s | (3-1) | R³ = H 120 | DMF 2 | POMI 43 μl | K₂CO₃ 61 mg | 1 | −30 | 31 | 43 |
| 33 | BOCNH | cyc-PnMe | H | POM | s | (3-1) | R³ = H 230 | DMF 3 | POMI 87 μl 1.2 eq | K₂CO₃ 89 mg | 0.7 | −30 | 38 | 105 |
| 34 | BOCNH | cyc-Pn | CH₂OCONH₂ | POM | s | (3-1) | R³ = H 236 | DMF 3 | POMI 78 μl 1.2 eq | K₂CO₃ 107 mg | 1 | −25 | 79 | 216 |
| 35 | BOCNH | MeO—Me | CH₂OCONH₂ | POM | s | (3-1) | R³ = H 371 | DMA 5 | POMI 120 μl 1.2 eq | K ethylhexanoate 0.54 ml | 1.5 | −7 | 43 | 195 |
| 36 | CbzNH | Et | H | POM | s | (3-1) | R³ = H 153 | DMF 3 | POMI 65 μl | K₂CO₃ 92 mg | 0.5 | −20 | 72 | 136 |
| 37 | OHCNH | Et | H | POM | s | (7-1) | R = H₂N 50 | — | HCOOH 26 μl | Ac₂O 66 μl | 0.5 | rt | 90 | 47 |
| 38 | ClCH₂CONH | Et | H | POM | s | (7-1) | R = H₂N 50 | DCM 1 | ClCH₂COCl 12 μl | pyridine 12 μl | 0.5 | −20 | 95 | 54 |
| 39 | NO₂PhCH=N | Et | H | POM | s | (7-1) | R = H₂N 50 | DCM 3 | O₂NC₆H₄CHO 23 mg | MeC₆H₄SO₃H 1 mg | 2.5 | 45 | 32 | 20 |

(Abbreviations)
Q' = cephem nucleus
Q' = side chain acid minus carboxy

What we claim is:

1. A 7β-[2-(2-amino-4-thiazolyl)alkenoylamino]-3-cephem-4-carboxylic acid pharmaceutically acceptable ester represented by the following formula:

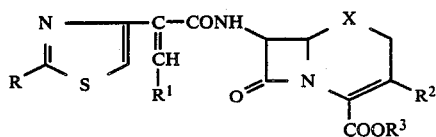

wherein
R is amino, X is sulfur, and
- $R^1$ is ethyl; $R^2$ is $CH_2OCH_2CH=CH_2$; and $R^3$ is pivaloyloxymethyl;
- $R^1$ is ethyl; $R^2$ is $CH_2OCH_2CH_2F$; and $R^3$ is pivaloyloxymethyl;
- $R^1$ is ethyl; $R^2$ is $CH_2OMe$; and $R^3$ is pivaloyloxymethyl;
- $R^1$ is ethyl; $R^2$ is $CH_2OCH(Me)_2$; and $R^3$ is pivaloyloxymethyl;
- $R^1$ is ethyl; $R^2$ is H; and $R^3$ is pivaloyloxymethyl;
- $R^1$ is methyl; $R^2$ is $CH_2OCONH_2$; and $R^3$ is pivaloyloxymethyl;
- $R^1$ is ethyl; $R^2$ is $CH_2OCONH_2$; and $R^3$ is pivaloyloxymethyl;
- $R^1$ is ethyl; $R^2$ is H; and $R^3$ is 1-ethoxycarbonyloxyethyl;
- $R^1$ is ethyl; $R^2$ is H; and $R^3$ is pivaloyloxyethyl;
- $R^1$ is ethyl; $R^2$ is H; and $R^3$ is acetoxyethyl;
- $R^1$ is ethyl; $R^2$ is H; and $R^3$ is acetoxymethyl;
- $R^1$ is methyl; $R^2$ is H; and $R^3$ is pivaloyloxymethyl;
- $R^1$ is ethyl; $R^2$ is $CH_2OCONH_2$; and $R^3$ is acetoxyethyl;
- $R^1$ is ethyl; $R^2$ is $CH_2OCONH_2$ and $R^3$ is 1-ethoxycarbonyloxyethyl; or
- $R^1$ is cyclopropylmethyl; $R^2$ is H; and $R^3$ is pivaloyloxymethyl.

2. The compound as claimed in claim 1 wherein R is amino; X is sulfur; $R^1$ is ethyl; $R^2$ is $CH_2OCH_2CH=CH_2$; and $R^3$ is pivaloyloxymethyl.

3. The compound as claimed in claim 1 wherein R is amino; X is sulfur; $R^1$ is ethyl; $R^2$ is $CH_2OCH_2CH_2F$; and $R^3$ is pivaloyloxymethyl.

4. The compound as claimed in claim 1 wherein R is amino; X is sulfur; $R^1$ is ethyl; $R^2$ is $CH_2OMe$; and $R^3$ is pivaloyloxymethyl.

5. The compound as claimed in claim 1 wherein R is amino; X is sulfur; $R^1$ is ethyl; $R^2$ is $CH_2OCH(Me)_2$; and $R^3$ is pivaloyloxymethyl.

6. The compound as claimed in claim 1 wherein R is amino; X is sulfur; $R^1$ is ethyl; $R^2$ is H; and $R^3$ is pivaloyloxymethyl.

7. The compound as claimed in claim 1 wherein R is amino; X is sulfur; $R^1$ is methyl; $R^2$ is $CH_2OCONH_2$; and $R^3$ is pivaloyloxymethyl.

8. The compound as claimed in claim 1 wherein R is amino; X is sulfur; $R^1$ is ethyl; $R^2$ is $CH_2OCONH_2$; and $R^3$ is pivaloyloxymethyl.

9. The compound as claimed in claim 1 wherein R is amino; X is sulfur; $R^1$ is ethyl; $R^2$ is H; and $R^3$ is -ethoxycarbonyloxyethyl.

10. The compound as claimed in claim 1 wherein R is amino; X is sulfur; $R^1$ is ethyl; $R^2$ is H; and $R^3$ is pivaloyloxyethyl.

11. The compound as claimed in claim 1 wherein R is amino; X is sulfur; $R^1$ is ethyl; $R^2$ is H; and $R^3$ is acetoxyethyl.

12. The compound as claimed in claim 1 wherein R is amino; X is sulfur; $R^1$ is ethyl; $R^2$ is H; and $R^3$ is acetoxymethyl.

13. The compound as claimed in claim 1 wherein R is amino; X is sulfur; $R^1$ is methyl; $R^2$ is H; and $R^3$ is pivaloyloxymethyl.

14. The compound as claimed in claim 1 wherein R is amino; X is sulfur; $R^1$ is ethyl; $R^2$ is $CH_2OCONH_2$; and $R^3$ is acetoxyethyl.

15. The compound as claimed in claim 1 wherein R is amino; X is sulfur; $R^1$ is ethyl; $R^2$ is $CH_2OCONH_2$ and $R^3$ is 1-ethoxycarbonyloxyethyl.

16. The compound as claimed in claim 1 wherein R is amino; X is sulfur; $R^1$ is cyclopropylmethyl; $R^2$ is H; and $R^3$ is pivaloyloxymethyl.

17. An oral antibacterial preparation containing an antibacterially effective amount of a compound claimed in claim 1.

* * * * *